(12) United States Patent
Masuta et al.

(10) Patent No.: US 11,629,351 B2
(45) Date of Patent: Apr. 18, 2023

(54) METHOD FOR SUPPRESSING METHYLATION OF TARGET DNA IN PLANT

(71) Applicant: NATIONAL INSTITUTE OF ADVANCED INDUSTRIAL SCIENCE AND TECHNOLOGY, Tokyo (JP)

(72) Inventors: Chikara Masuta, Sapporo (JP); Tsuyoshi Inukai, Sapporo (JP); Wataru Matsunaga, Sapporo (JP); Reika Isoda, Sapporo (JP); Takeshi Matsumura, Sapporo (JP); Go Atsumi, Sapporo (JP)

(73) Assignee: NATIONAL INSTITUTE OF ADVANCED INDUSTRIAL SCIENCE AND TECHNOLOGY, Tokyo (JP)

( * ) Notice: Subject to any disclaimer, the term of this patent is extended or adjusted under 35 U.S.C. 154(b) by 0 days.

(21) Appl. No.: 17/262,507

(22) PCT Filed: Jul. 25, 2019

(86) PCT No.: PCT/JP2019/029318
§ 371 (c)(1),
(2) Date: Jan. 22, 2021

(87) PCT Pub. No.: WO2020/022461
PCT Pub. Date: Jan. 30, 2020

(65) Prior Publication Data
US 2021/0292779 A1 Sep. 23, 2021

(30) Foreign Application Priority Data
Jul. 25, 2018 (JP) .............................. JP2018-139316

(51) Int. Cl.
*C12N 15/82* (2006.01)
(52) U.S. Cl.
CPC ......... *C12N 15/8218* (2013.01); *C12N 15/82* (2013.01); *C12N 2830/46* (2013.01)
(58) Field of Classification Search
None
See application file for complete search history.

(56) References Cited

U.S. PATENT DOCUMENTS

2016/0002654 A1   1/2016   Matsumura et al.
2016/0017348 A1 * 1/2016   Jacobsen ............ C12N 15/8216
                                                      536/23.6

FOREIGN PATENT DOCUMENTS

WO        2014/129560 A1      8/2014
WO        2017/219027 A1     12/2017
WO     WO-2017219027 A1 *    12/2017   ......... C12N 15/8509

OTHER PUBLICATIONS

Au et al, 2017, Genes, 8:1-24.*
Shibuya et al, 2009, PNAS, 106:1660-1665.*
Dong et al, 2021, BMC Plant Biology, In review/Preprint.*
Matsunaga et al, 2019, BMC Plant Biology, 19:1-13.*
Kanazawa et al, 2011, The Plant Journal, 65:156-168.*
Matzke et al, 2014, Nature Reviews Genetics, 15:394-408.*
Bussiere et al, 2003, Plant Biotechnology Journal, 423-435.*
Gallego-Bartolome, 2018, PNAS, 115:E2125-E2134.*
International Search Report dated Oct. 21, 2019 corresponding to PCT/JP2019/029318 filed Jul. 25, 2019; 2 pages. English translation.
Written Opinion of the International Search Authority dated Oct. 21, 2019 corresponding to PCT/JP2019/029318 filed Jul. 25, 2019; 6 pages. English translation.
Bussiere, Frederic et al., "Development of an efficient cis-trans-cis ribozyme cassette to inactivate plant genes," *Plant Biotechnol. J.* (2003; accepted Jul. 4, 2003) 1:423-435.
Gallego-Bartolome, Javier et al, "Targeted DNA demethylation of the *Arabidopsis* genome using the human TET1 catalytic domain," *PNAS* (2018; published online Feb. 14, 2018); 115(9):E2125-E2134.
Gallusci, Philippe et al., "Epigenetics for Plant Improvement: Current Knowledge and Modeling Avenues," *Trends in Plant Science* (Jul. 1, 2017) 22(7):610-623.
Liu, Getong et al., "Re-characterization of hammerhead ribozymes as molecular tools for intermolecular RNA cleavage," *Organic & Biomolecular Chemistry* (2017; accepted May 9, 2017) 15:4681-4685.
Matsunaga, W. et al, "A technique to reduce dna methylation in a sequence-specific manner by using a ribozyme-expressing cucumber mosaic virus vector," *Phytopatholgy* (2018; published online Oct. 15, 2018) 108(10S):S1.15-S1.16.
Matsunaga, Wataru et al., "Transcriptional silencing of 35S driven-transgene is differentially determined depending on promoter methylation heterogeneity at specific cytosines in both plus- and minus-sense strands," *BMC Plant Biology* (2019; published online Jan. 14, 2019) 19(24):1-13.
Matzke, Marjori A. et al., "RNA-directed DNA methylation: an epigenetic pathway of increasing complexity," *Nature* (Jun. 2014; corrected online Jul. 18, 2014); 15:394-408.
Otagaki, Shungo et al., "Rapid induction of transcriptional and post-transcriptional gene silencing using a novel Cucumber mosaic virus vector," *Plant Biotechnology* (2006; accepted Feb. 9, 2006) 23:259-265.
Philips, Joshua G. et al., "The widely used *Nicotiana benthamiana* 16c line has an unusual T-DNA integration pattern including a transposon sequence," *PLOS ONE* (Feb. 23, 2017) 9 pages.
Puerta-Fernandez, Elena et al., "Ribozymes: recent advances in the development of RNA tools," *FEMS Microbiology Reviews* (2003; first published online Mar. 7, 2003); 27:75-97.
Bharti et al. (Sep. 2015) AtROS1 Overexpression Provides Evidence for Epigenetic Regulation of Genes Encoding Enzymes of Flavonoid Biosynthesis and Antioxidant Pathways During Salt Stress in Transgenic Tobacco, *Journal of Experimental Botany*, 66(19):5959-5969.

(Continued)

*Primary Examiner* — Jason Deveau Rosen
(74) *Attorney, Agent, or Firm* — Mintz Levin Cohn Ferris Glovsky and Popeo, P.C.

(57) ABSTRACT

Plants are created with desired traits by conveniently and rapidly inhibiting methylation of target DNA in plants, without using recombination technology. Scaffold RNA produced by transcription of target DNA is cleaved in an RNA-directed DNA methylation mechanism.

6 Claims, 14 Drawing Sheets

Specification includes a Sequence Listing.

(56) References Cited

OTHER PUBLICATIONS

Courtial et al. (Mar. 2001, (published online Nov. 15, 2000)) "Tnt1 Transposition Events are Induced by in Vitro Transformation of *Arabidopsis Thaliana*, and Transposed Copies Integrate into Genes", *Molecular Genetics and Genomics*, 265(1):32-42.
Cui et al. (Jan. 2013) "Tnt1 Retrotransposon Mutagenesis: A Tool for Soybean Functional Genomics", *Plant Physiology*, 161(1):36-47.
Duangpan et al. (Sep. 2013) "Insertional Mutagenesis using Tnt1 Retrotransposon in Potato", *Plant Physiology*, 163(1):21-29.
Kiselev et al. (Feb. 2015) "Salicylic Acid Induces Alterations in the Methylation Pattern of the VaSTS1, VaSTS2, and VaSTS10 Genes in Vitis Amurensis Rupr, Cell Cultures", *Plant Cell Reports*, 34(2):311-320.
Mazier et al. (May 9, 2007) "Successful Gene Tagging in Lettuce Using the Tnt1 Retrotransposon from Tobacco", *Plant Physiology*, 144:18-31.
Mohanasundaram et al. (Jun. 2019 (published online Jan. 28, 2019)) "*Agrobacterium*-Mediated Tnt1 Mutagenesis of Moss Protonemal Filaments and Generation of Stable Mutants with Impaired Gametophyte", *Molecular Genetics and Genomics*, 294(3):583-596.
Zhang et al. (Mar. 27, 2018) "Efficient Transposition of the Retrotransposon Tnt1 in Cucumber" *Horticultural Plant Journal*, 4(3):111-116.
Zhao et al. (May 5, 2010) "An NAC Transcription Factor Orchestrates Multiple Features of Cell Wall Development in *Medicago Truncatula*", *The Plant Journal*, 63:100-114.
Erdmann, et al. (Oct. 8, 2020) "RNA-directed DNA Methylation", PLOS Genetics, 16(10):e1009034. (31 pages.).

\* cited by examiner

FIG. 4

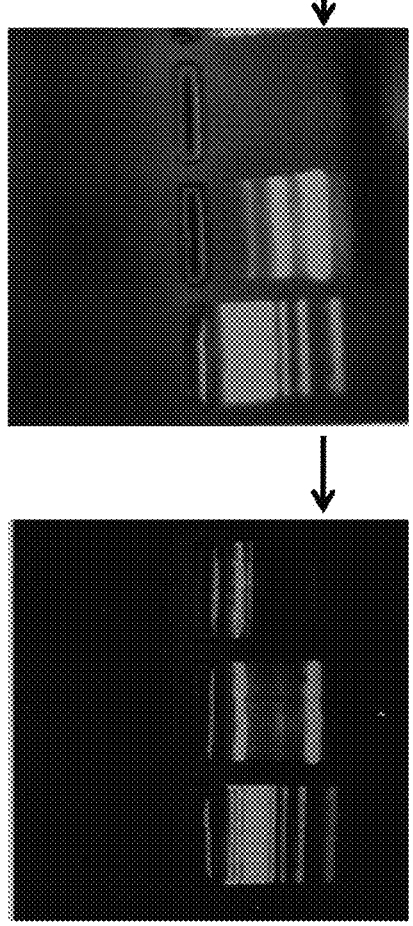

35S promoter sequence

CCAAAGGGCAATTGAGACTTTTCAACAAAGG
GTAATATCCGGAAACCTCCTCGGATTCCATT
GCCCAGCTATCTGTCACTTTATTGTGAAGAT
AGTGGAAAAGGAAGGTGGCTCCTACAAATGC
CATCATTGCGATAAAGGAAAGGCCATCGTTG
AAGATGCCTCTGCCGACAGTGGTCCCAAAGA
TGGACCCCACCCACGAGGAGCATGTGGAA
AAAGAAGACGTTCCAACCACGTCTTCAAAGC
AAGTGGATTGATGTGATATCTCCACTGACGT
AAGGGATGACGCACAATCCCACTATCCTTCG
CAAGACCCTTCCTCTATATAAGGAAGTTCAT
TTCATTTGGAGAGAACACGGG (SEQ ID NO:1)

FIG. 5

Target sequence of ribozyme

GUC targets of ribozyme within 35S promoter (single-stranded) sequence and surrounding sequences are indicated by underlines (DNA sequences)

35S promoter (single-stranded) (+1 to -344; +1:transcription initiation site)

5'-
(+1)TCTCTCCAAATGAAATGAACTTCCTTATATAGAGGAAGGGTCTTGCGAAGGATAGTGGATTG
TGCGTCATCCCTTACGTCAGTGGAGATCACATCAATCCACTGCTTGAAGACGTGGTTGGAAC
GTCTCTTTTCCACGATGCTCCTCGTGGGGTCCATCTTTGGGACCACTGTGGGCAGAGG
CATCTTCAAGGATGGCCTTTCCTTATCGCAATGATGGCATTTGTAGGAGCCACCTTCCTTTTCCACT
ATCTTCACAATAAAGTGACAGATAGCTGGGCAATGGAATCCGAGGAGGTTTCCGGATATTACCCTT
TGTTGAAAAGTCTCAAT(-344)
-3' (SEQ ID NO:2)

Ribozyme sequence

CGAGGCCTGATCTCCACTCTGATGAGTCCGTGAGGACGAAACGTAAGGACGCGTGCG (SEQ ID NO:3)

<u>AGGCCT</u>   StuI restriction site
<u>ACGCGT</u>   MluI restriction site

FIG. 8

GUC targets of ribozyme within 35S promoter (+strand) sequence and surrounding sequences are indicated by underlines (DNA sequences)

35S promoter (+strand) (-385 to -1; +1: transcription initiation site)

5'-
(-385)CTCTAGAGGATCCCCCTCAGAAGACCAGAGGGCTATTGAGACTT
TTCAACAAAGGTAATATCGGGAAACCTCCTCGGATTCCATTGCCCAG
CT<u>ATCGTCACTTCA</u>CTTGCGATAAAAGGACAGTAGAAAAGGAAGGTGGCTCCT
ACAAATGCCATCATTGCGATAAAAGGCTATCGTTCAAGATGCCT
CTACCGACA<u>GTGTCCCAAAG</u>ACGTTCCAACCACCCCACCGAGGAACATCG
TGGAAAAGAAGAGACGTTCCAA<u>CCACGTCTTCAAA</u>GCAAGTGGATTGAT
GTGATATCTCCACTGACGTAAGGGATGACGCACAATCCCACTATCCTT
CGCAAGACCCTTCCTCTATATAAGGAAGTTCATTTCATTTGGAGAGGAC
AGG(-1)
-3' (SEQ ID NO:5)

<u>TATCTGTCACTTCA</u>  A
<u>CAGTGGTCCCAAAG</u>  B
<u>ACCACGTCTTCAAA</u>  C

FIG. 9

AAGCTTCTTTTTTCTTCTTCGTTCATACAGTTTTTTTGTTATCAGCTTACATT
TTCTTGAACCGTAGCTTTCGTTTTCTTTTTTAACTTTCCATTCGGAGTTTTGTATC
TTGTTTCATAGTTTGTCCCAGGATTAGAATGATTAGGCATCGAACCTTCAAGAATTTG
ATTGAATAAAACATCTTCATTCTTAAGATATGAAGATAATCTTCAAAAGGCCCCTGGG
AATCTGAAAGAGAAGAGGAGCAGGCCCATTTATATGGGAAAGAACAATAGTATTCTTAT
ATAGGCCCATTTAAGTTGAAAAACAATCTTCAAAAGTCCCACATCGCTTAGATAAGAAA
ACGAAGCTGAGTTTATATACAGCTAGAGCTCGAAGTCGATTGggCGGACCGTTGACG
AAACGCGAAAGCGTCTAGCGGAAAGCTACTGATGAGTCGACCGATGAAGTCTGATGAG
TCCGAAAGGACGAAACAGATAGCCGGACCGTTGACGAAACGCGAAAGCGTCTAGCGA
AAGCTACTGATGAGTCGACCTTTGGCTGATGAGTCGACGAAGGACGAAACCACTGTCC
GGACCGTTGACGAAACGCGAAAGCGTCTAGCGGAAAGCGTGGTTGGGACCGTTGACGCTTT
GAACTGATGAGTCGGAAAGCTACGGAAAGCTACTGATGAGTCGACGAAACGGCGAAA
GCGTCTAGCGAAAGCTACTGATGAGTCGACctTTTTTTTGAGCTC (SEQ ID NO:6)

AAGCTT HindIII restriction site
U6 promoter
Ribozyme 35S(+)A2BC
U6 terminator
GAGCTC SacI restriction site

METHOD FOR SUPPRESSING METHYLATION OF TARGET DNA IN PLANT

FIELD

The present invention relates to a method for inhibiting methylation of target DNA in plants.

BACKGROUND

Gene expression in plants is regulated by DNA methylation and chemical modification of histones, which are collectively known as epigenetic control. It occurs by the mechanism of RNA silencing, with RNA silencing being largely divided into two types: post-transcriptional gene silencing (PTGS) and transcriptional gene silencing (TGS). Plants depend on epigenetic control for regulation of levels of accumulation of functional components, and techniques for freely manipulating epigenetics are necessary to cause accumulation of useful components at high levels in plants. However, epigenetic control has been considered too complex to allow specific removal of methylation from target DNA.

The technology for directing demethylation to specific DNA sequences is virtually non-existent, with only one technique for directing demethylation using dCAS-fused TET1 finally being reported in recent years (NPL 1). However, using dCAS-fused TET1 to direct demethylation requires recombinant technology, which means that demethylation cannot be directed in a convenient and rapid manner.

CITATION LIST

Patent Literature

[PTL 1] International Patent Publication No. WO2014/129560

Non-Patent Literature

[NPL 1] Gallego-Bartolome J et al., Proceedings of the National Academy of Sciences of the United States of America 55, E2125-E2134 (2018)
[NPL 2] Gallusci P et al., Trends in Plant Science 22, 610-623 (2017)
[NPL 3] Matzke M. A and Mosher R. A, Nature Reviews Genetics 15, 394-408 (2014)
[NPL 4] Puerta-Fernandez E et al., FEMS Microbiology Reviews 27, 75-97 (2003)
[NPL 5] Liu G et al., Organic & Biomolecular Chemistry 15, 4681-4685 (2017)
[NPL 6] Bussiere F et al., Plant Biotechnology Journal 1, 423-435 (2003)
[NPL 7] Otagaki S et al., Plant Biotechnology 23, 259-265 (2006)
[NPL 8] Matsunaga W et al., BMC Plant Biology 19, 24 (2019)
[NPL 9] Philips J. G et al., PloS one, 12, e0171311 (2017)

SUMMARY

Technical Problem

It is an object of the present invention to create plants with desired traits by conveniently and rapidly inhibiting methylation of target DNA in plants, either using recombinant technology or without using recombinant technology.

Solution to Problem

As a result of avid research on the object stated above, the present inventors have found, surprisingly, that in an RNA-directed DNA methylation mechanism, cleavage of scaffold RNA produced by transcription of target DNA, and especially cleavage of the scaffold RNA by expression of one or more ribozymes specific for the scaffold RNA in the plant cells, allows methylation of the target DNA in the plants to be specifically inhibited.

Specifically, the main gist of the present invention is as follows.

(1) A method for inhibiting methylation of target DNA in plant cells, wherein the method comprises cleaving scaffold RNA produced by transcription of the target DNA in an RNA-directed DNA methylation mechanism.

(2) The method according to (1), wherein the step of cleaving the scaffold RNA is carried out by causing expression of one or more ribozymes specific for the scaffold RNA in the plant cells.

(3) The method according to (2), wherein expression of the one or more ribozymes is transient.

(4) The method according to any one of (1) to (3), wherein the target DNA is a promoter that controls a gene that expresses a desired trait for plant cells.

(5) The method according to (4), wherein the gene that expresses the desired trait is a gene coding for the amino acid sequence of an enzyme that controls synthesis or accumulation of a plant-derived functional component.

(6) The method according to any one of (1) to (5), wherein expression of the one or more ribozymes in plant cells is carried out by a plant virus vector method, an agroinfiltration method, a magnICON® system or a particle gun method.

(7) The method according to any one of (1) to (6), wherein the plant cells are non-isolated cells of a plant body.

(8) The method according to any one of (1) to (6), wherein the plant cells are cultured cells.

(9) A method for creating a plant with a desired trait, wherein the method comprises using the method according to any one of (1) to (8) to inhibit methylation of DNA that contributes to expression of a desired trait for plants.

(10) A method for producing a plant-derived functional component, wherein the method comprises using the method according to any one of (1) to (8) to inhibit methylation of DNA that contributes to synthesis or accumulation of a plant-derived functional component, thereby causing accumulation of the functional component in the plant cells, and recovering the functional component from the plant cells.

(11) An expression system for accumulation of a plant-derived functional component, wherein the expression system comprises:

(A) a plant body or plant cells that produce scaffold RNA produced by transcription of DNA that contributes to synthesis or accumulation of the plant-derived functional component, in an RNA-directed DNA methylation mechanism, and (B) one or more ribozymes specific for the scaffold RNA.

(12) A ribozyme expression vector that comprises a nucleotide sequence coding for one or more ribozymes specific for scaffold RNA produced by transcription of target DNA, in an RNA-directed DNA methylation mechanism.

(13) The ribozyme expression vector according to (12), wherein a nucleotide sequence coding for a different self-cleaving ribozyme is adjacent to the 3' and 5'-ends of the nucleotide sequence coding for the ribozyme specific for the scaffold RNA.

(14) The ribozyme expression vector according to (13), wherein the nucleotide sequence coding for the ribozyme specific for the scaffold RNA is the trans form, and the nucleotide sequence coding for the different self-cleaving ribozyme is the cis form.

(15) Use of a ribozyme expression vector according to any one of (12) to (14) for creation of a plant having a desired trait.

(16) Use of a ribozyme expression vector according to any one of (12) to (14) for production of a plant-derived functional component.

Advantageous Effects of Invention

According to the present invention it is possible to inhibit methylation of target DNA in plants, thereby allowing convenient and rapid specific control of TGS of the target DNA. It is thereby possible to obtain plants with desired traits, thus greatly contributing to production of useful proteins or increased accumulation levels of functional components in plants.

BRIEF DESCRIPTION OF DRAWINGS

FIG. 3a shows the cucumber mosaic virus A1 vector (CMV-A1) RNA2 with the 35S promoter sequence. FIG. 3b shows *N. benthamiana* 16C line inoculated with CMV-A1 vector carrying the 35S promoter sequence. FIG. 3c shows DNA methylation rates in progeny obtained from *N. benthamiana* 16C line inoculated with CMV-A1 vector carrying the 35S promoter sequence.

FIG. 4 shows the 35S promoter sequence and the detection results for scaffold RNA produced from the 35S promoter. The bands indicated by the arrows are the detected scaffold RNA. The single- and double-underlined portions of the 35S promoter sequence indicate the regions corresponding to the plus strand and minus strand of the detected scaffold RNA.

FIG. 5 shows the sequence of a ribozyme-targeted 35S promoter, and the sequence of the ribozyme.

FIG. 7a shows GFP fluorescence in 208 Rz(−) S2. FIG. 7b shows DNA methylation rates in 208 Rz(−) S2. FIG. 7c shows DNA methylation pattern in the 35S promoter region of 208 Rz(−) S2. In FIG. 7c, the region with particularly reduced DNA methylation near the transcription initiation site is framed.

FIG. 8 shows the target sequence for an *Arabidopsis thaliana* transfer ribozyme. The GUC at 3 locations on the plus strand of the 35S promoter scaffold RNA are indicated as A, B and C.

FIG. 9 shows the sequence of the ribozyme 35S (+)A2BC cassette which was integrated in *Arabidopsis thaliana*.

DESCRIPTION OF EMBODIMENTS

[1. Background]

Gene expression in plants is regulated by epigenetic control. The term "epigenetics" means a change in genetic function or mechanism without any change to the DNA sequence, but still transmitted via cellular division. DNA methylation is known as one type of mechanism of epigenetics (NPL 2). The reaction comprises either methyl group-addition reaction at the 5-position carbon atom of the pyrimidine ring of cytosine or the 6-position nitrogen atom of the purine ring of adenine, but it is believed that gene expression in plants is mainly controlled by methylation of cytosine. Specifically, methylation and demethylation of cytosine in DNA switches gene expression on and off without changing the nucleotide sequence information itself. Suppression of gene expression by DNA methylation is known as transcriptional gene silencing (TGS).

The present invention is based on the foundational concept that artificially controlling epigenetic regulation in plants allows alteration to desired plant phenotypes without gene recombination.

Great advances have been made in understanding DNA methylation in *Arabidopsis thaliana* as a model plant. In plants, methylation takes place at the CpG, CpHpG and CpHpH sites (H representing a nucleotide other than guanine), and DRM2, MET1, CMT3 and CMT2 are known as the main DNA methyltransferase enzymes that transfer and covalently bond methyl groups to DNA. DNA methyltransferases are currently classified into the two types of de novo enzymes that create new methyl labeling on DNA, and: maintenance enzymes that recognize methylation locations on the DNA parent strand and transmit the new methylation to the daughter chain after DNA replication, and only DRM2 is known to be a de novo DNA methyltransferase. While it is not clearly understood how the locations for de novo DNA methylation are determined by cells, previous evidence suggests that the mechanism of RNA-directed DNA methylation (RdDM) is involved for most locations.

As mentioned above, the present invention is based on the knowledge that in an RNA-directed DNA methylation mechanism, cleavage of scaffold RNA produced by transcription of target DNA, and especially cleavage of the scaffold RNA by expression of one or more ribozymes specific for the scaffold RNA in the plant cells, allows methylation of target DNA in the plants to be specifically inhibited. The RNA-directed DNA methylation mechanism and ribozymes used for the present invention will therefore be explained first.

[1-1. RdDm Mechanism]

Figure 1:
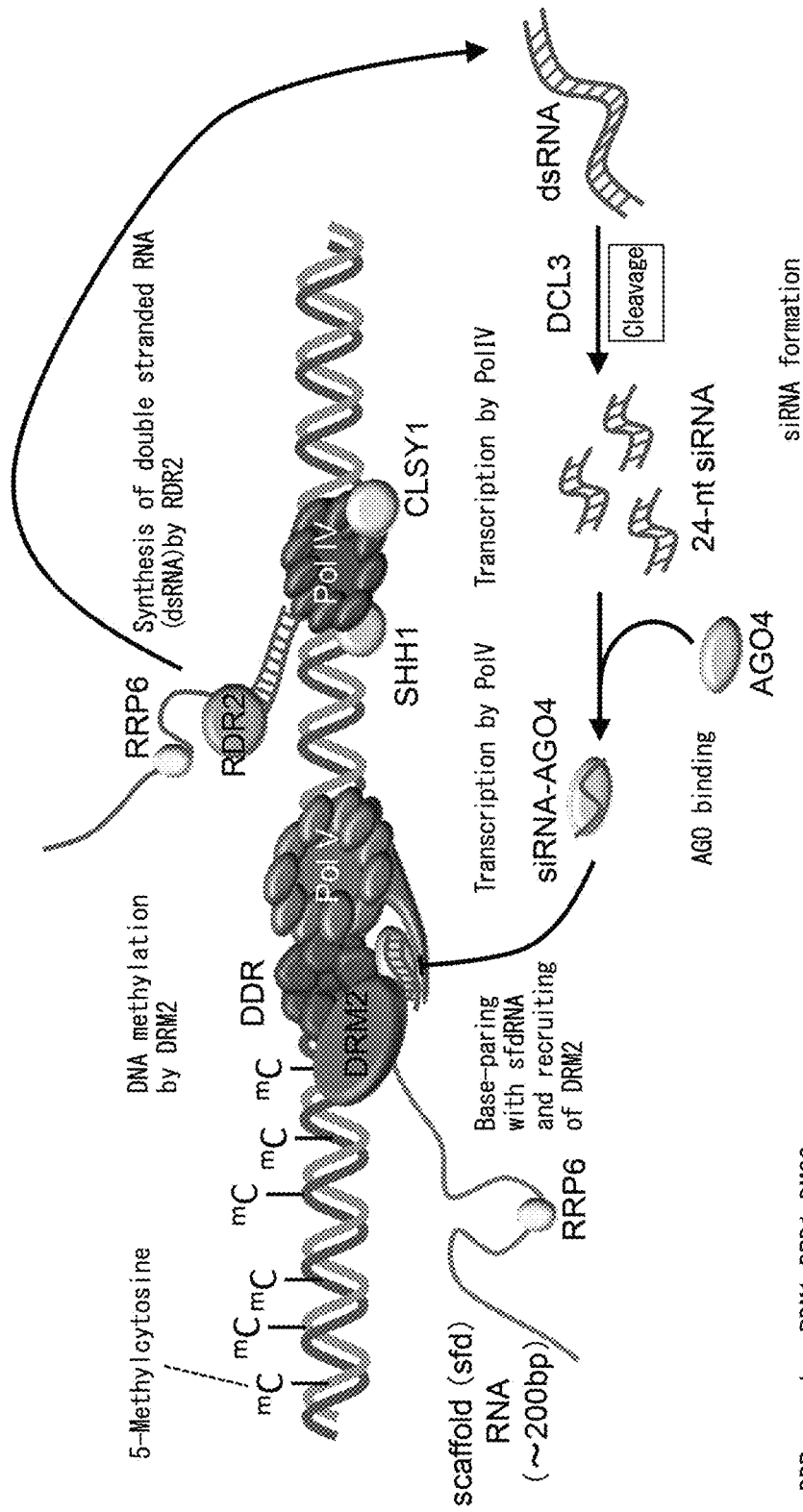
FIG. 1 shows a DNA methylation model in an RdDM pathway.

In the RdDM mechanism, as shown in FIG. 1, first PolIV is recruited to the methylation target genome region and the RNA of the target region is transcribed. The PolIV transcription product is converted there to double-stranded RNA by RNA-Dependent RNA Polymerase 2 (RDR2), and cleaved into 24-nucleotide siRNA by the RNaseIII-like enzyme Dicer-Like 3 (DCL3) (NPL 3). The siRNA is modified by methylation at the 3'-end by HUA Enhancer 1 (HEN1) and then taken up into Argonaut 4 (AGO4) to form a silencing effector complex. Complementary siRNA taken up into the silencing effector complex forms base pairs with RNA transcribed by DNA-dependent RNA polymerase V (PolV) (hereunder referred to as "scaffold RNA"), and recruits the complex. Domains Rearranged Methyltransferase (DRM2), as de novo methyltransferase in the DNA region corresponding to the siRNA is then recruited through the silencing effector complex, and methylates the DNA. It is thought that RNA-Directed DNA Methylation 1 (RDM1), Defective In RNA-Directed DNA Methylation 1 (DRD1) and Defective In Meristem Silencing 3 (DMS3), which have the ability bind to AGO4, DRM2 and methylated DNA, play important roles in recruiting.

Figure 2:
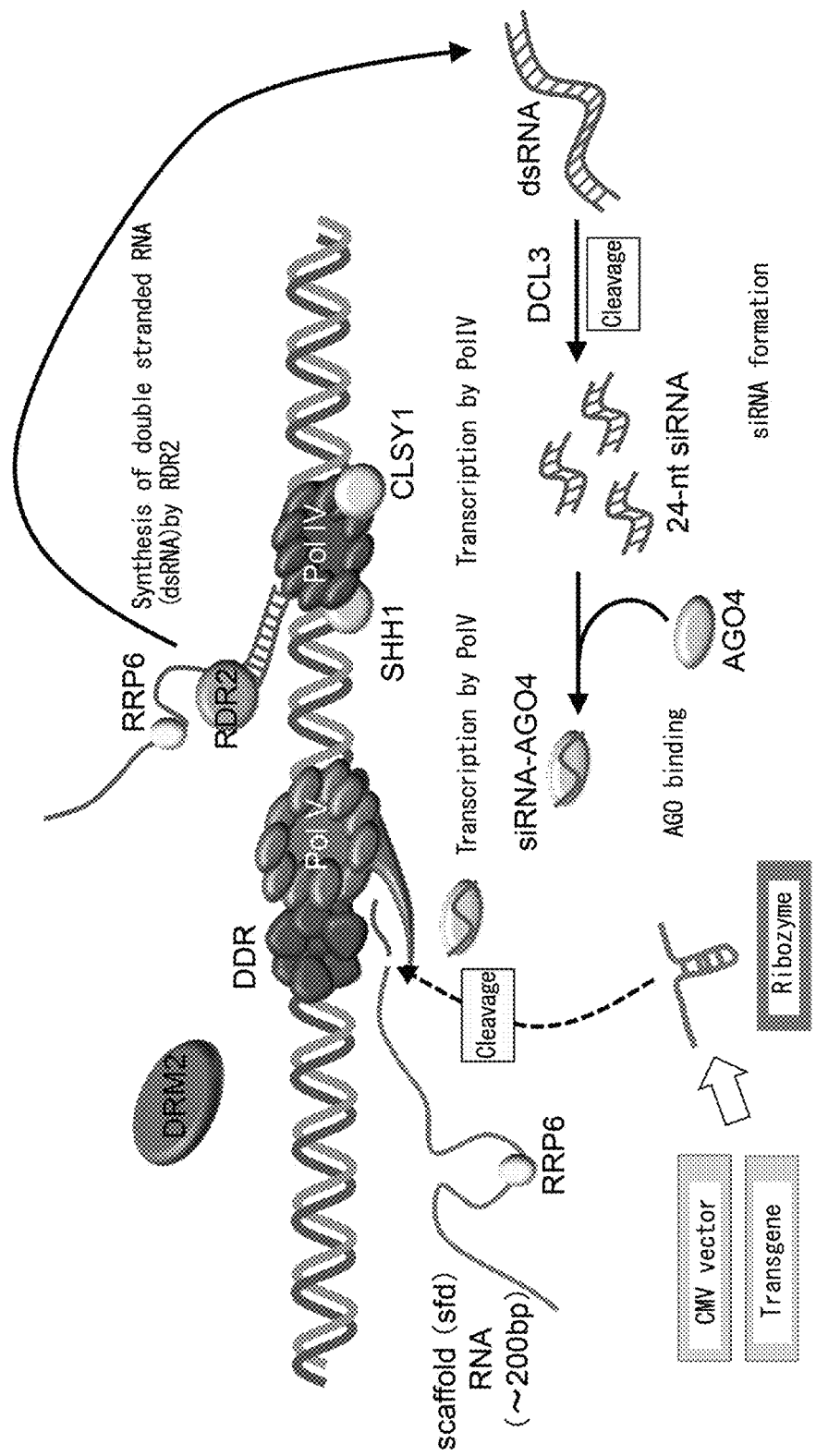
FIG. 2 shows a DNA demethylation model via cleavage of scaffold RNA by a ribozyme.

The RNA transcribed by PolIV and PolV from the target DNA (which have essentially the same sequences since they are transcribed from the same region, although the RNA transcribed by PolV is referred to specifically as "scaffold RNA"), have functions in the RdDM pathway for formation of siRNA and for bringing methyltransferase DRM2 into target DNA. As shown in FIG. 2, the targeted DNA is specified by the sequences of the scaffold RNA and the siRNA bound to it, and therefore if specific scaffold RNA is cleaved and removed from the pathway, then only methylation of DNA corresponding to the scaffold RNA will be inhibited, resulting in progression toward demethylation. In contrast, inhibiting the functions of other proteins associated with the RdDM pathway is undesirable as it completely disrupts the RdDM pathway and is harmful to the plant.

The scaffold RNA is restricted in terms of cleavage site sequences since it must comprise sequences with high cleavage efficiency by ribozymes, such as GUC, GUA and GUU (NPL 1), with otherwise free selection of the cleavage sites so long as this condition is satisfied.

[1-2. Ribozyme]

One possible method for removing the scaffold RNA is to send large amounts of antisense RNA to the nucleus to scavenge the scaffold RNA. When antisense RNA forms double strands with the target, however, it can lead to formation of siRNA, potentially having the reverse effect of promoting TGS. The present inventors carried out further research in light of this knowledge, and as a result, we have recently succeeded in inhibiting methylation of target DNA in plants by cleaving scaffold RNA using certain ribozymes which are applied for cleavage of RNA viruses that are intracellularly produced in large amounts. Since the ribozymes only have 8-base complementarity with the scaffold RNA, they do not form double-strands and do not generate siRNA.

Ribozymes are special RNA molecules having enzyme activity that cleaves nucleic acid sequences in a site-specific manner, and much active research has been conducted on their structures and functions since their discovery in 1981. This has led to elucidation of enzyme activity site structures (shapes and nucleic acid sequences), making it now possible, using chemical synthesis, to obtain ribozymes that specifically cleave any desired sequence sites, and that have come to be utilized in a large variety of fields. The ribozymes to be used for the invention are not particularly restricted so long as they are able to cleave and degrade scaffold RNA produced by transcription of target DNA, in a sequence-specific manner. Such ribozymes can be designed by methods known to those skilled in the art. The types of known ribozymes that cleave target RNA in vivo include hammerhead ribozymes, hairpin ribozymes and pseudoknot ribozymes, with hammerhead ribozymes being used in particular as the basis for developing functional RNA. Hammerhead ribozymes are able to cleave RNA phosphodiester bonds at specific sites, and they are used by creating the smallest hammerhead ribozyme trans form based on the natural hammerhead ribozyme to inhibit target gene expression in vivo by RNA-mediated gene regulation. A hammerhead ribozyme is composed of a center active region comprising a conserved core sequence having catalytic activity (helix II), and recognition regions comprising two hybrid-forming arm sequences that recognize target sequences, at the 3'-end and 5'-end of the active region (helix III and helix I) (NPL 4). A target-specific hammerhead ribozyme can be made by converting the hybrid-forming arm sequence for the target RNA, according to simple Watson-Crick base pairing rules. Hammerhead ribozymes with different core sequences for target RNA can be designed, and by using a sequence in a system complementary to a hybrid-forming sequence around triplets specific for the target RNA, it is possible to bond to the target RNA and cleave the phosphodiester bond at the 3'-end of the triplet.

The sequence required as the substrate for the ribozyme is a triplet with U as the 2nd nucleotide, with DWH (D=A/U/G, W=A/U, H=A/U/C) being particularly easy to cleave (NPL 5). Therefore, if a portion is synthesized so as to find a DWH sequence on target RNA and to be complementary to the sequences at both ends, then that portion will be an RNA-cleaving enzyme that cleaves the target RNA at the 3'-end of DWH. Based on homology with the target sequence of scaffold RNA, therefore, a person skilled in the art can freely design a ribozyme able to cleave and degrade it in a sequence-specific manner.

According to the invention, therefore, a DNA sequence that contributes to expression of a desired trait in a plant and is controlled by methylation is selected as a cleavage site for design of a ribozyme targeting it.

[2. Method for Controlling Methylation of Target DNA in Plant Cells]

According to one aspect of the invention there is provided a method for inhibiting methylation of target DNA in plant cells, the method comprising cleaving scaffold RNA produced by transcription of the target DNA in an RNA-directed DNA methylation mechanism.

By specifically cleaving scaffold RNA that is the trigger for DNA methylation that suppresses expression of a desired trait in a plant, recruiting of DRM2 to the region of the DNA corresponding to the siRNA is inhibited, thereby specifically inhibiting methylation of the target DNA in the plant. Specific cleavage of the scaffold RNA is carried out, for example, by introducing one or more ribozymes specific for the scaffold RNA into the plant cells, and causing expression of the one or more ribozymes in the plant cells.

The target DNA is not particularly restricted so long as it is DNA contributing to expression of the desired trait in plants and controlled by methylation, and as an example, it may be a promoter that controls a gene for expression of a desired trait for plant cells. Examples of desired traits include properties observed in the outer appearance (form) such as shape, color and size, and observable physiological properties such as the flowering period, as well as other physiological properties such as resistance to pathogenic organisms and temperature, but preferred properties are those relating to accumulation of functional components (metabolic components) in plants. The gene that expresses the desired trait is therefore preferably a gene coding for the amino acid sequence of an enzyme that controls synthesis or accumulation of a plant-derived functional component.

Examples of plant-derived functional components include acetylene, thiophenes, glycosides, glucosinates, purines, pyrimidines, alkaloids, phenolics (such as quinones), essential oils, vitamins, terpenoids (such as iridoids, sesquiterpenes, diterpenoids and triterpenoids), lignans and flavonoids.

Expression of the ribozyme in the plant cells is preferably carried out using recombination technology, or using a transient expression system for convenience and speed. Examples are the plant virus vector method, agroinfiltration method, magnICON®, system and particle gun method, as well as combinations thereof.

In the plant virus vector method, cDNA of a plant virus genome with the target DNA inserted is transcribed in vitro, the obtained RNA is used to inoculate as vector onto a plant for infection, and then the viral multiplication and systemic movement is used for the expression of a target gene in the plant. This method expresses the target gene utilizing the auto-replicating ability of the virus, and therefore the expression level of the target gene in each plant cell can be increased by using a vector based on CMV or TMV, which have especially high proliferation potency.

In agroinfiltration, a culture solution of an *Agrobacterium* transformed with a target gene-inserted T-DNA vector is introduced into plant tissue by a physical method (such as syringe injection or depressurized permeation), to infect the plant, thereby causing transient expression of the target gene in the plant. With this method it is possible to translocate and systemically infect a plant body with highly infectious *Agrobacterium* using a physical method (injection or permeation), thus causing uniform expression of the target gene throughout the tissue of the plant. *Agrobacterium* is a general name for a pathogenic group of bacteria among *Rhizobium*, a gram-negative soil bacterium genus, with examples of *Agrobacterium* including *Agrobacterium tumifaciens* which is associated with root tumors. When an *Agrobacterium*-derived vector is used for transient expression of an exogenous gene in a plant, the vector is usually introduced into the plant tissue by a physical method (syringe injection or depressurized permeation), to infect the plant. Since an *Agrobacterium*-derived vector has strong infectivity by acting on the T-DNA region, using it for infection in a uniform systemic manner in the plant body by a physical method (injection or permeation) allows an exogenous gene to be expressed uniformly and evenly throughout the tissue of the plant.

In a magnICON® system, TMV or PVX genomic cDNA having a target gene inserted is introduced into a T-DNA vector, and a culture solution of the *Agrobacterium* transformed with the obtained T-DNA vector is introduced into plant tissue by a physical method (syringe injection or depressurized permeation) to infect the plant, thereby causing transient expression of the target gene in the plant. In other words, the vector can be spread out systemically through the plant body by physical means (injection or permeation) to produce infection, thereby causing expression of the target gene throughout the entire tissue of the plant. Since the target gene is expressed by utilizing the auto-replicating ability of a virus (TMV or PVX), it is possible to increase the expression level of the target gene in each plant cell. This method, therefore, combines the advantages of a plant virus vector method and agroinfiltration method.

In addition, a nucleic acid molecule comprising a sequence corresponding to the RNA2 genome of cucumber mosaic virus (CMV) in which all or part of the gene coding for the 2b protein has been replaced with an exogenous gene, in functional combination with the T-DNA sequence of *Agrobacterium*, may be introduced into a host plant that functionally expresses the RNA1 genome and RNA3 genome of CMV, as well as protein 2b, and the plant may be cultivated to express the exogenous gene, thereby allowing the exogenous gene to be spread and expressed uniformly in all of the cells of the plant body while also increasing the efficiency of expression of the exogenous gene in the cells, so that high expression can be achieved throughout the entire plant body (PTL 1). This method can be employed as a technique suitable for the magnICON® system using TMV or PVX, and makes it possible to increase the degree of freedom for types of host plants and introducible exogenous gene sizes.

In the particle gun (or particle bombardment) method, fine particles of a metal such as gold or tungsten coated with DNA or a vector are ejected at high speed to introduce the target DNA into cells.

The ribozyme expression vector used for the invention is not particularly restricted so long as it comprises a nucleotide sequence coding for one or more ribozymes that are specific for scaffold RNA produced by transcription of target DNA, and can cause expression of the ribozymes in plant cells, but it will typically be a plant virus vector or T-DNA vector, and most preferably a plant virus vector. Plant virus vectors are not particularly restricted so long as they can penetrate into the nucleus of plant cells, and they include vectors derived from single-stranded RNA viruses such as Tobacco mosaic virus (TMV), Cucumber mosaic virus (CMV), Potato X virus (PVX) and Clover yellow vein virus (ClYVV), single-stranded DNA viruses such as Bean yellow dwarf virus (BeYDV), Beet curly top virus (BCTV), Cabbage leaf-curl virus (CaLCuV), Wheat dwarf virus (WDV) and Tomato yellow leaf curl China virus (TYLCCNV), and double-stranded DNA viruses such as Cauliflower mosaic virus (CaMV). Particularly preferred among these are vectors derived from the RNA virus Cucumber mosaic virus (CMV), among which CMV-A1 vector is an example.

The species of plants to which the present invention may be applied are not particularly restricted, but typical plants include those of Poaceae, Leguminosae, Brassicaceae, Compositae, Solanaceae, Rosaceae, Cucurbitaceae and Convolvulaceae. Examples of preferred plants include alfalfa, barley, green bean, canola, cowpea, cotton, corn, clover, lotus, lentil, lupin, millet, oat, pea, peanut, rice, rye, sweet clover, sunflower, sweet pea, soybean, sorghum, triticale, jicama, velvet bean, horse-bean, wheat, *Wisteria*, nut plants, thale cress, redtop grass, Welsh onion, snapdragon, dutch celery, peanut, asparagus, *Atropa*, wild oat, thorny bamboo, rape, bromegrass, rurimagaribana, *Camellia, Cannabis, Capsicum*, chickpea, goosefoot, chicory, citrus, coffee tree, juzudama, cucumber, pumpkin, bermudagrass, *Dactylis,* jimsonweed, *Digitalis*, yam, oil palm, ooshiba, fescue, strawberry, geranium, soybean, sunflower, Hemerocallidoideae, Para rubber plant, henbane, sweet potato, lettuce, *Lens culinaris*, lily, flax, ryegrass, lotus, tomato, marjoram, apple, mango, *Manihot*, burr medic, African toadflax, tobacco, *Onobrychis*, geranium, Chinese fountain grass, *Petunia, Phleum*, meadow grass, cherry flower, buttercup, radish, currant, castor bean, raspberry, sugarcane, *Salpiglossis, Senecio, Setaria*, white mustard, eggplant, sorghum, buffalo grass, cacao, clover, *Trigonella caerulea* and grape.

The plant cells may be in any form, such as non-isolated cells present in the plant body, or cultured cells from tissue culture isolated from the plant body. In the case of cultured cells, they may be differentiated cells, dedifferentiated cells, or redifferentiated cells.

[3. Method for Creating Plant with Desired Trait]

The method for inhibiting methylation of target DNA may be used to inhibit methylation of DNA that contributes to expression of a desired trait for a plant, in order to create a plant having the desired trait. According to a second aspect of the invention, therefore, there is provided a method for creating a plant with a desired trait, wherein the method comprises using the method described above to inhibit methylation of DNA that contributes to expression of a desired trait for plants.

[4. Method for Producing Plant-Derived Functional Component]

The method for inhibiting methylation of target DNA may also be used to inhibit methylation of DNA that contributes to synthesis and accumulation of a plant-derived functional component in order to produce the plant-derived functional component in a convenient and rapid manner. According to a third aspect of the present invention, therefore, there is provided a method for producing a plant-derived functional component, wherein the method described above is used to inhibit methylation of DNA that contributes to synthesis or accumulation of the plant-derived functional component in order to accumulate the functional component in the plant cells, and the functional component is recovered from the plant cells, as well as an expression system for synthesis or accumulation of a plant-derived functional component, wherein the expression system comprises (A) a plant body or plant cells that produce scaffold RNA produced by transcription of DNA that contributes to synthesis or accumulation of the plant-derived functional component, in an RNA-directed DNA methylation mechanism, and (B) one or more ribozymes specific for the scaffold RNA.

[5. Ribozyme Expression Vector]

According to a fourth aspect of the present invention there is provided a ribozyme expression vector that comprises a nucleotide sequence coding for one or more ribozymes specific for scaffold RNA produced by transcription of target DNA, in an RNA-directed DNA methylation mechanism. As explained above, the ribozyme expression vector can be used to create a plant having a desired trait, and/or to produce a plant-derived functional component.

The ribozyme expression vector of the invention may have a structure wherein a nucleotide sequence coding for a different self-cleaving ribozyme is adjacent to the 3' and 5'-ends of the nucleotide sequence coding for the ribozyme specific for the scaffold RNA. If the nucleotide sequence coding for the ribozyme specific for the scaffold RNA is the trans form and the nucleotide sequence coding for the different self-cleaving ribozyme is the cis form, then a monomer of the target ribozyme will be cut out by the self-cleaving ribozyme (NPL 6). By inserting multiple trans form target ribozymes between cis form ribozymes in this manner it is possible to increase the expression level of the same target ribozyme or to simultaneously express different target ribozymes.

The ribozyme expression vector may also comprise a promoter and/or terminator operationally linked to the nucleotide sequences coding for one or more ribozymes specific for the scaffold RNA and the different self-cleaving ribozyme adjacent to its 3' and 5'-ends.

The promoter is not particularly restricted so long as it allows the ribozyme to be expressed in plant cells, and examples include U6 promoter, cauliflower mosaic virus (CaMV) 35S promoter, cassava mosaic virus promoter, figwort mosaic virus promoter, Badnavirus promoter, Strawberry vein binding virus (SVBV) promoter, Mirabilis mosaic virus promoter (MMV), Rubisco promoter, actin promoter and ubiquitin promoter. U6 promoter is preferred among these.

The terminator is also not particularly restricted so long as it allows the ribozyme to be expressed in plant cells, and examples include U6 terminator, *Agrobacterium* nos terminator or heat shock protein (hsp) terminator, and Cauliflower mosaic virus (CaMV) 35S terminator.

The present invention will now be explained in greater detail by the following examples. It is to be understood, however, that the invention is not restricted in any way to the following embodiments, and various modifications thereof may be implemented.

EXAMPLES

[Experiment 1] Inducing DNA Methylation by CMV-A1 Vector Comprising Partial Sequence of 35S Promoter (1) Construction of CMV-A1 Vector Comprising Partial Sequence of 35S Promoter.

Figure 3:
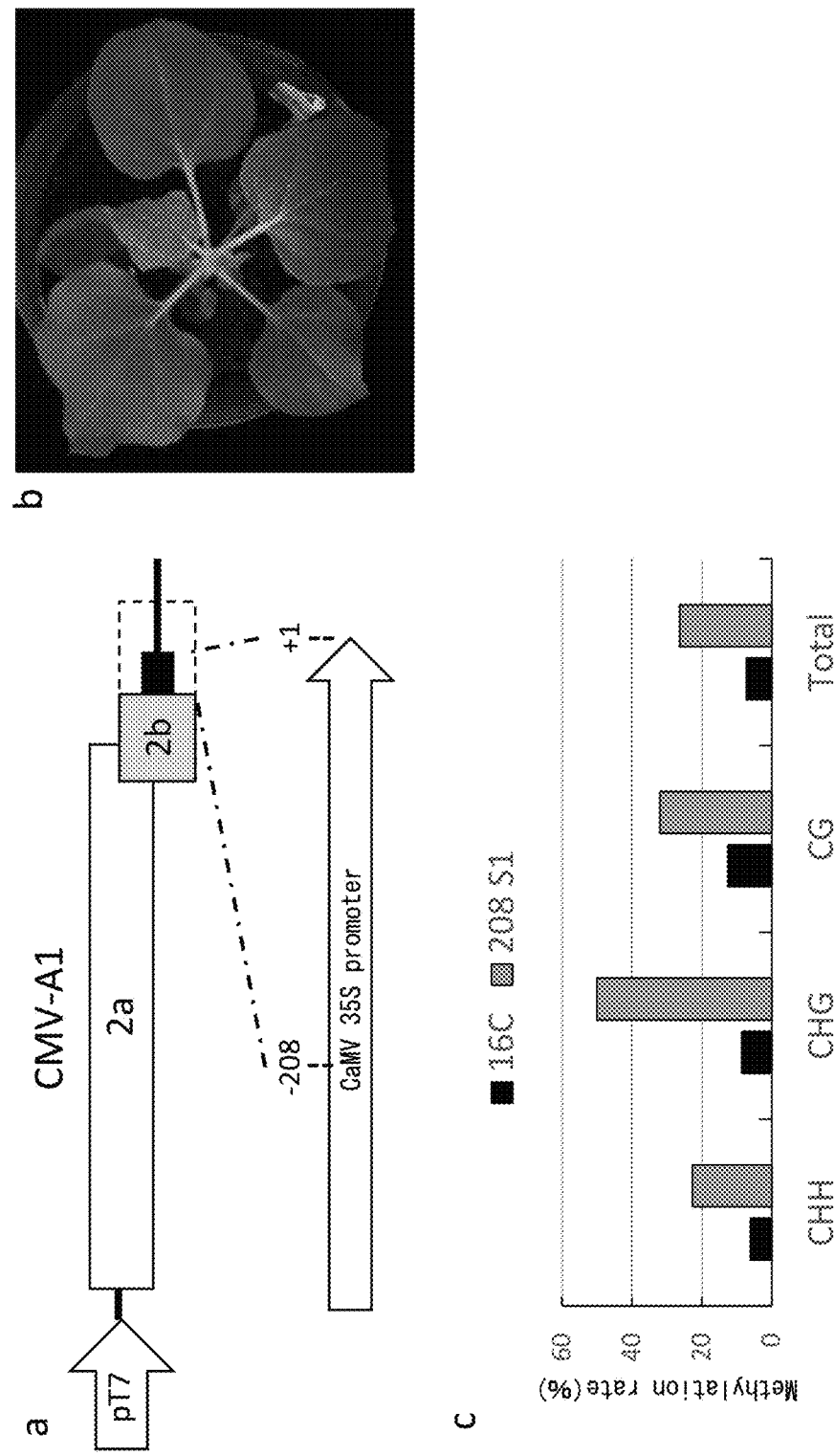
FIG. 3a-c show a method for constructing a CMV-A1 vector comprising the 35S promoter sequence, and the 35S promoter DNA methylation rates in progeny (208 S1) obtained by inoculating the vector onto the GFP-expressing *N. benthamiana* line (16C).

A sequence was artificially synthesized having StuI and MluI restriction sites added at the end of a partial sequence of 35S promoter, from the transcription initiation site to 208 bp upstream (35S-208), and it was incorporated into the infectious cDNA clone plasmid cloning sites (StuI and MluI restriction sites) of CMV-A1 vector (see NPL 7), using a common method (FIG. 3a). The 35S-208 sequence was constructed by PCR amplification and cloning using pBI121 (Clontech). The full length of the 35S promoter in pBI121 is 345 bases, with 35S-208 being the amplified and cloned portion of 208 bases including the as-1 site (see NPL 8).

(2) Inoculation of 35S-208-Incorporated CMV-A1 onto the 16C Line.

The 35S-208-incorporated CMV-A1 vector (RNA2) was transcribed in vitro using T7 RNA polymerase. It was then combined with RNA1 and RNA3 that had been transcribed in vitro with the CMV-Y RNA1 infectious clone pCY1 and the RNA3 infectious clone pCY3, and mechanically inoculated into the line 16C (see NPL 9) (FIG. 3b). Individuals lacking GFP fluorescence due to TGS were selected among the 16C individuals infected with CMV, and their seeds were harvested after flowering. Individuals derived from the seeds were designated as 208 S1.

(3) DNA Methylation in 35S Promoter Region of 208 S1.

DNA was extracted from the leaves of 16C and 208 S1 using an Illustra DNA Extraction Kit Nucleon Phytopure (GE Healthcare), and the extracted DNA was subjected to bisulfite treatment using an EZ DNA Methylation-Lightning Kit (Zymo Research), converting the non-methylated cytosine to uracil. A TaKaRa EpiTaq HS for bisulfite-treated DNA (TaKaRa) was used for PCR amplification of the 35S promoter region from the bisulfite-treated DNA. The PCR primers used were 35S-346F-bisuT (5'-ATTGAGAYTTT-TYAAYAAAGGGTA-3': SEQ ID NO: 7) and 35S+1A-bisuA (5'-CTCTCCAAATGAAATGAACTTC-3': SEQ ID NO: 8). The obtained PCR product was ligated to pTAC1 vector using a Dyna Express TA PCR Cloning Kit (Bio Dynamics Laboratory). This was then used for transformation of E. coli JM109 Competent Cells (TaKaRa), and the proliferated plasmids were extracted. The extracted plasmids were sequenced by a common method. As a result of comparing the frequency of methylation of cytosine in the 35S promoter region between 16C and 208 S1 for the CG, CHG (H=A/C/T) and CHH sites, based on sequencing results, it was confirmed that methylation of cytosine had been induced by 208 S1 at all of the sites (FIG. 3c).

[Experiment 2] Detecting 35S Promoter Scaffold RNA

In order to detect the scaffold RNA transcribed from 35S promoter, RNA was extracted from the leaves of the 208 S1 line using RNAzol RT (Molecular Research Center), and a SuperScript III First Strand Synthesis SuperMix (Invitrogen) was used for the following RT-PCR on the total extracted RNA. First, primers T7-35S-5-345 (5'-ATTGA-GACTTTTCAACAAAG-3': SEQ ID NO: 9) for detection of the RNA plus strand and 35S+1R (5'-GTTCTCTC-CAAATGAAATGAAC-3': SEQ ID NO: 10) for detection of the minus strand were used for RT reaction, and then the primer pair T7-35S-5-345 and 35S-3-130 (5'-GCAGAGG-CATCTTCAACGATG-3': SEQ ID NO: 11) for detection of the plus strand and the primer pair 35S-5-160 (5'-CCACC-CACGAGGAGCATCGTG-3': SEQ ID NO: 12) and 35S+1R for detection of the minus strand were used for PCR. As a result of RT-PCR, an amplification product comprising both the plus strand and minus strand was obtained, and since their sequences matched the sequences of 35S promoter (FIG. 4), this confirmed that transcription from both the plus strand and minus strand of 35S promoter had taken place.

[Experiment 3] Construction of Ribozyme-Expressing CMV Vector (1) Ribozyme Design
The ribozyme target sequence and ribozyme sequence are shown in FIG. 5. The results of Experiment 2 confirmed that scaffold RNA of the plus strand and minus strand had been transcribed from the 35S promoter region, but since GUC which is the most easily cleaved among the triplets of the ribozyme substrate is abundantly present in the minus strand scaffold RNA, a ribozyme was designed for the minus strand scaffold RNA. The target GUC selected was GUC at 79 bp upstream from the transcription initiation site, in consideration of the GC content and presence of repeats in the ribozyme-binding sequence, and the ribozyme was designed to cleave this GUC.
(2) Creation of Ribozyme-Expressing CMV Vector
For synthesis and cloning of double-stranded DNA coding for the ribozyme designed in (1), oligo DNA 35S (−)-5RZ-45(5'-CGAGGCCTGATCTCCACTCTGAT-GAGTCCGTGAGGACGAAACGTA-3': SEQ ID NO: 13) and 35S (−)-3RZ-32(5'-CGCACGCGTCCT-TACGTTTCGTCCTCACGGAC-3': SEQ ID NO: 14) were synthesized, each with StuI and MluI restriction sites added to the 5'-end, and a double strand was produced with these using PCR. This was incorporated into the infectious cDNA clone plasmid cloning site of CMV-A1 vector (the StuI and MluI restriction sites) by a common method.

Figure 6:
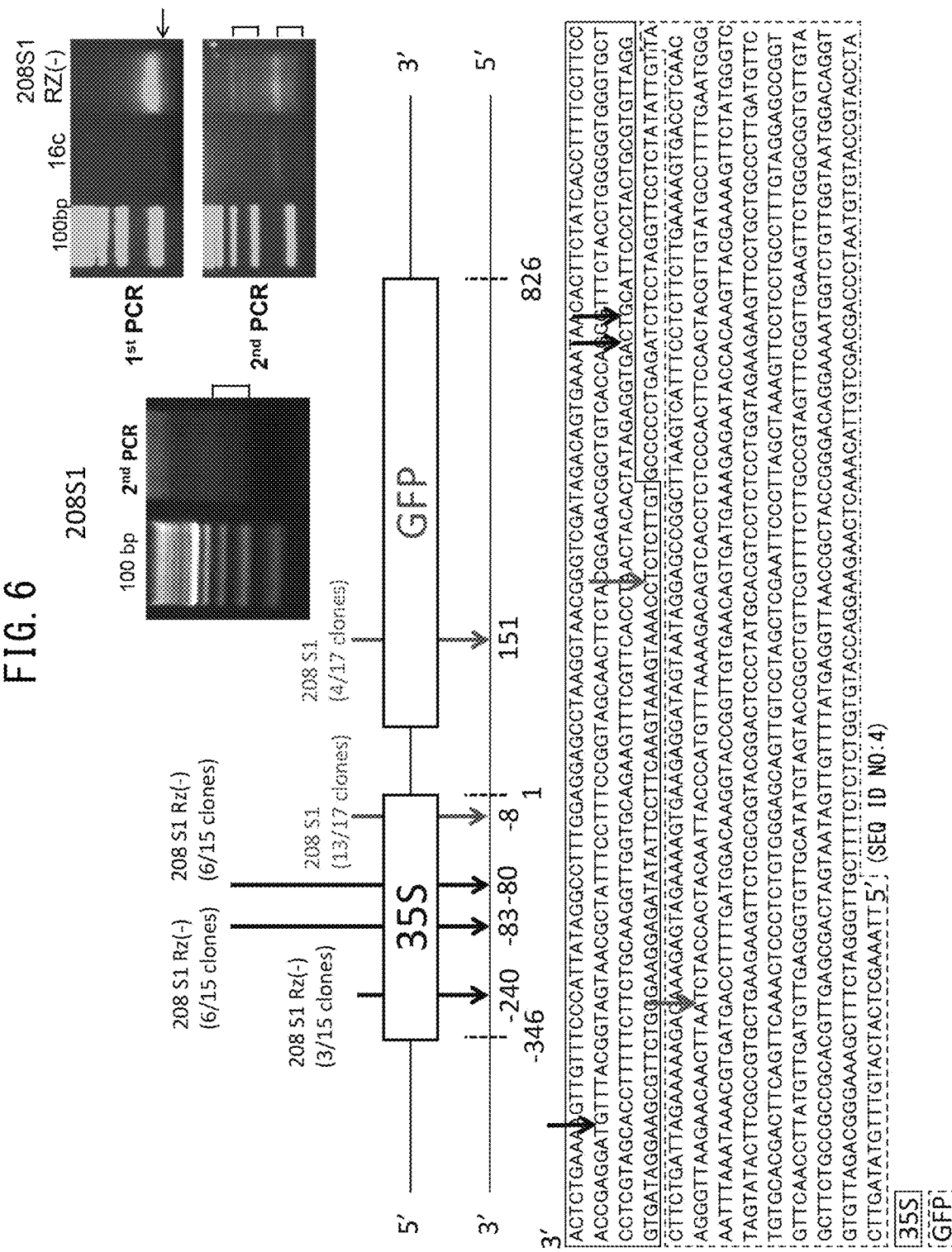
FIG. 6 shows ribozyme-cleaved locations at the 5'-end of scaffold RNA. The black arrows indicate the cleavage locations in a ribozyme-expressing individual (208 S1 Rz), and the gray arrows indicate the cleavage locations in a control (208 S1).

[Experiment 4] Identification of Scaffold RNA Cleavage Location by Ribozyme (1) Inoculation of Ribozyme-Incorporating CMV-A1 into 208 S1 Line.
The ribozyme-incorporated CMV-A1 vector (RNA2) was transcribed in vitro using T7 RNA polymerase. This was combined with RNA1 and RNA3 transcribed in vitro by the CMV-Y RNA1-infectious clone pCY1 and RNA3-infectious clone pCY3, and mechanically inoculated into a 208 S1 line. Methylation of 208 S1 was induced in the 35S promoter, resulting in TGS of the GFP gene. S1 is the self-pollinated first-generation of the TGS individual.
(2) Identification of Cleavage Location on Scaffold RNA Minus Strand
Using RNAzol RT (Molecular Research Center), RNA was extracted from the leaves of a healthy 208 S1 individual (208 S1) and a 208 S1 individual (208 S1 Rz(−)) that had been infected with ribozyme-expressing CMV-A1 vector, and the extracted total RNA was used for 5' RACE to identify the 5'-end sequence of the minus strand of the scaffold RNA. 5' RACE was carried out using a 5'/3' RACE Kit, 2nd Generation (Roche). The 5'-end of the 208 S1 scaffold RNA minus strand used as a control was detected at 8 bp upstream from the transcription initiation site of the GFP gene in 13 of the 17 clones, and at 151 bp downstream from the GFP transcription initiation site in 4 clones (FIG. 6). These results indicated that transcription of the scaffold RNA minus strand comprising the 35S promoter region was initiated from within the GFP gene. Also, the 5'-end was detected at locations 80 bp upstream from the GFP transcription initiation site in 6 of the 15 clones with the 208 S1 Rz(−) individual, 83 bp upstream in 6 clones and at 240 bp in 3 clones (FIG. 6). Since the locations are downstream from the transcription initiation location on the scaffold RNA minus strand in the control, this suggested ribozyme cleavage of the scaffold RNA minus strand in the 208 S1 Rz(−) individual. It is expected that demethylation of the 35S promoter was induced in the 208 S1 Rz(−) individual by cleavage of the scaffold RNA minus strand. Next, self-pollinated seeds were propagated from the 208 S1 Rz(−) individual, and DNA methylation of the 35S promoter region was analyzed in the next-generation (208 Rz(−)S2) that was not infected with the virus (Experiment 5).

Figure 7:
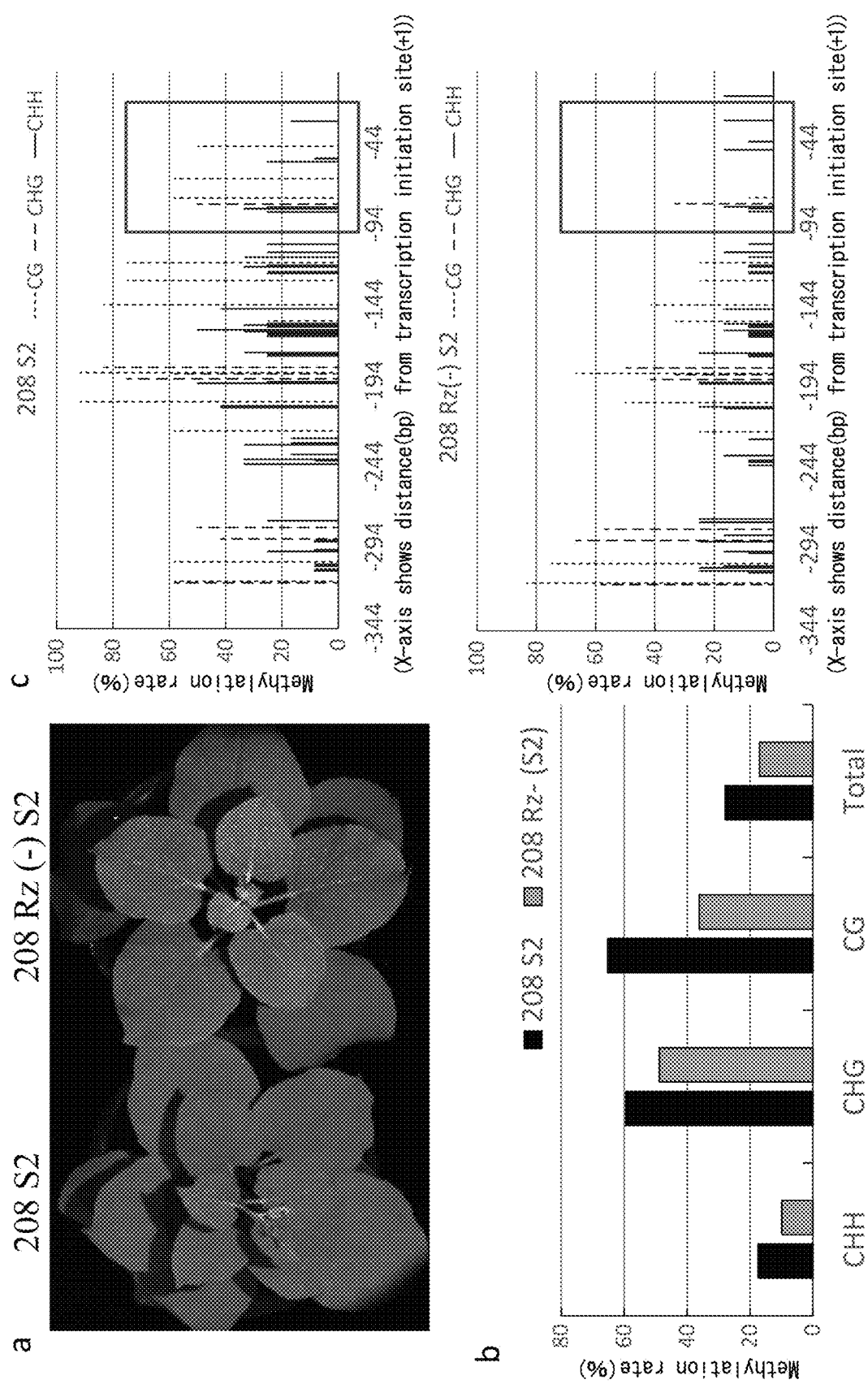
FIG. 7a-c show GFP fluorescence and 35S promoter region methylation in the progeny of *N. benthamiana* infected with the CMV vector expressing a ribozyme.

[Experiment 5] GFP Fluorescence and 35S Promoter Region Methylation in the Progeny of the 16C Line where a Ribozyme was Expressed by the CMV Vector Upon comparing GFP fluorescence in 208 Rz(−) S2 and the next-generation of the control 208 S1 (208 S2), GFP fluorescence was found to be restored in the ribozyme-expressing benthamiana progeny by CMV vector (FIG. 7a). Since GFP fluorescence was restored in 208 Rz(−) S2 compared to 208 S2, the frequency of cytosine methylation in the 35S promoter region was analyzed by the same method as in Experiment 1 (3). As a result, the frequency of methylation was found to be reduced at all of the sites of CG, CHG and CHH in 208 Rz(−) S2 compared to 208 S2 (FIG. 7b). Based on the pattern of methylation in the 35S promoter region, demethylation was especially notable near the transcription initiation site in 208 Rz(−)S2 (FIG. 7c). These results demonstrated that scaffold RNA can be cleaved by ribozyme expressed by CMV vector, inducing demethylation of the 35S promoter region to allow increased expression of the GFP gene, and that the state of demethylation in the 35S promoter region induced by this method is stably passed on to subsequent generations.

Figure 10:
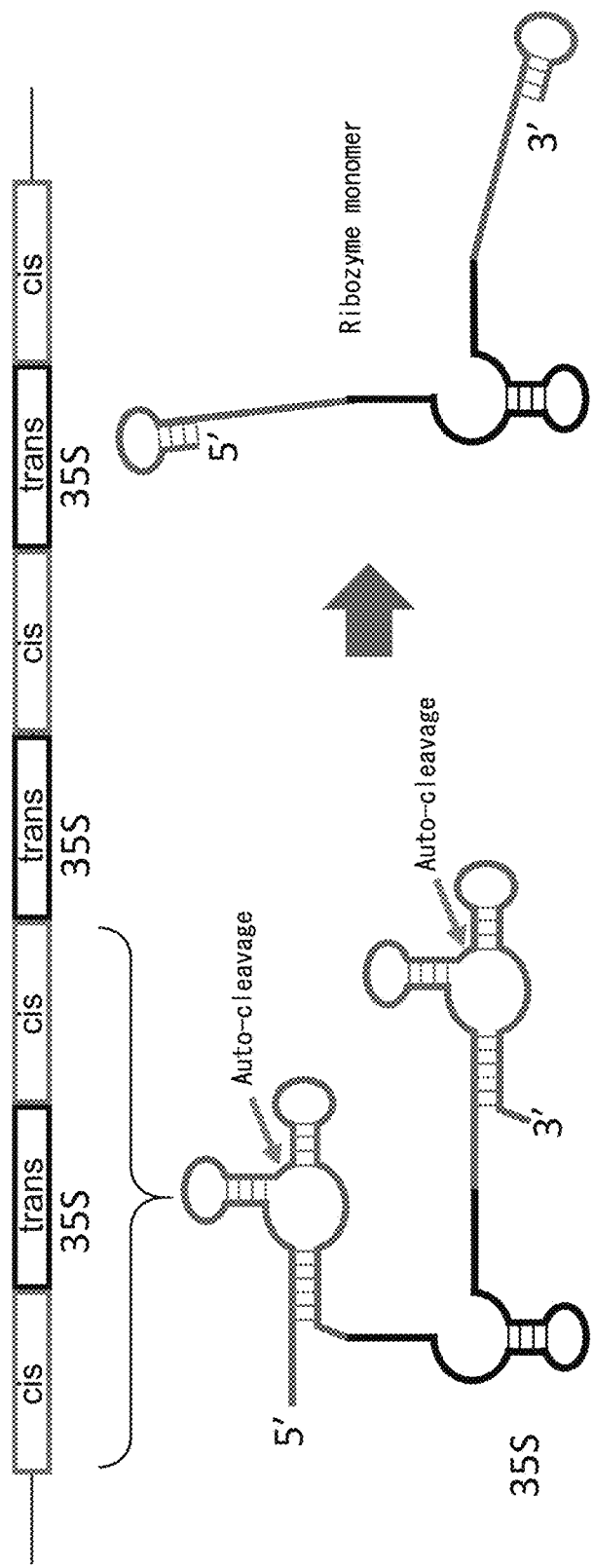
FIG. 10 shows the cis-trans-cis ribozyme structure and the self-cleaving site of the cis-form ribozyme.

[Experiment 6] Construction of *Arabidopsis thaliana* Expressing a Ribozyme (1) Ribozyme Design The ribozyme target sequence and ribozyme cassette sequence are shown in FIG. 8 and FIG. 9. A cis-trans-cis ribozyme was designed for simultaneous cleavage of GUC at 3 locations (designated as A, B and C) on the scaffold RNA plus strand of the 35S promoter. As shown in FIG. 10, the cis-trans-cis ribozyme has a structure in which a ribozyme that cleaves the target sequence in a trans manner (trans form) is flanked by auto-cleaving ribozymes (cis forms), each individual trans-form ribozyme exhibiting activity as a monomer by auto-cleavage by the adjacent cis-form ribozyme. A trans form ribozyme that cleaves GUC at locations A, B and C, each flanked with cis forms, was thus designed (ribozyme 35S (+)-A2BC).

(2) Creation of Ribozyme Expression Plasmid Vector

Figure 11:
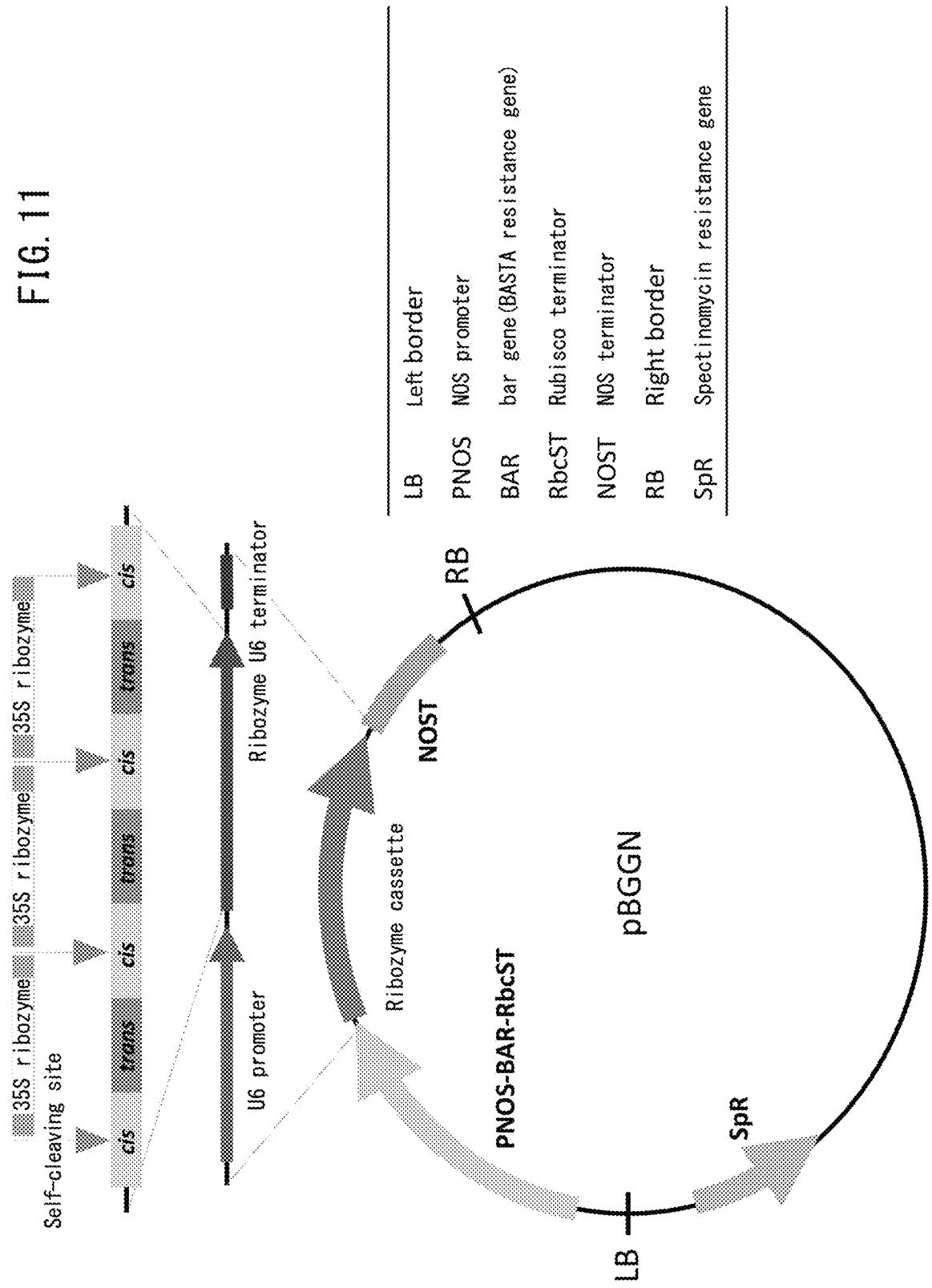
FIG. 11 shows the structure of the expression vector pBGGN used for transformation of *Arabidopsis thaliana*.

Double-stranded DNA was artificially synthesized having U6 promoter added at the 5'-end of the DNA sequence of ribozyme 35S (+)-A2BC designed in (1) and U6 terminator at the 3'-end, and further having HindIII and SacI restriction sites added at both ends (FIG. 9). This was incorporated into the cloning site (HindIII and SacI restriction sites) of expression vector pBGGN (Implanta Innovations, Inc.) by a common method (FIG. 11). The BASTA resistance gene (bar gene) was incorporated as a selective marker into pBGGN vector, and a 0.01% BASTA solution was sprayed onto the plant body to allow screening of plant transformants.

[Experiment 7] In Vitro Cleavage Activity of the Ribozyme Integrated in *Arabidopsis thaliana*

Figure 12:
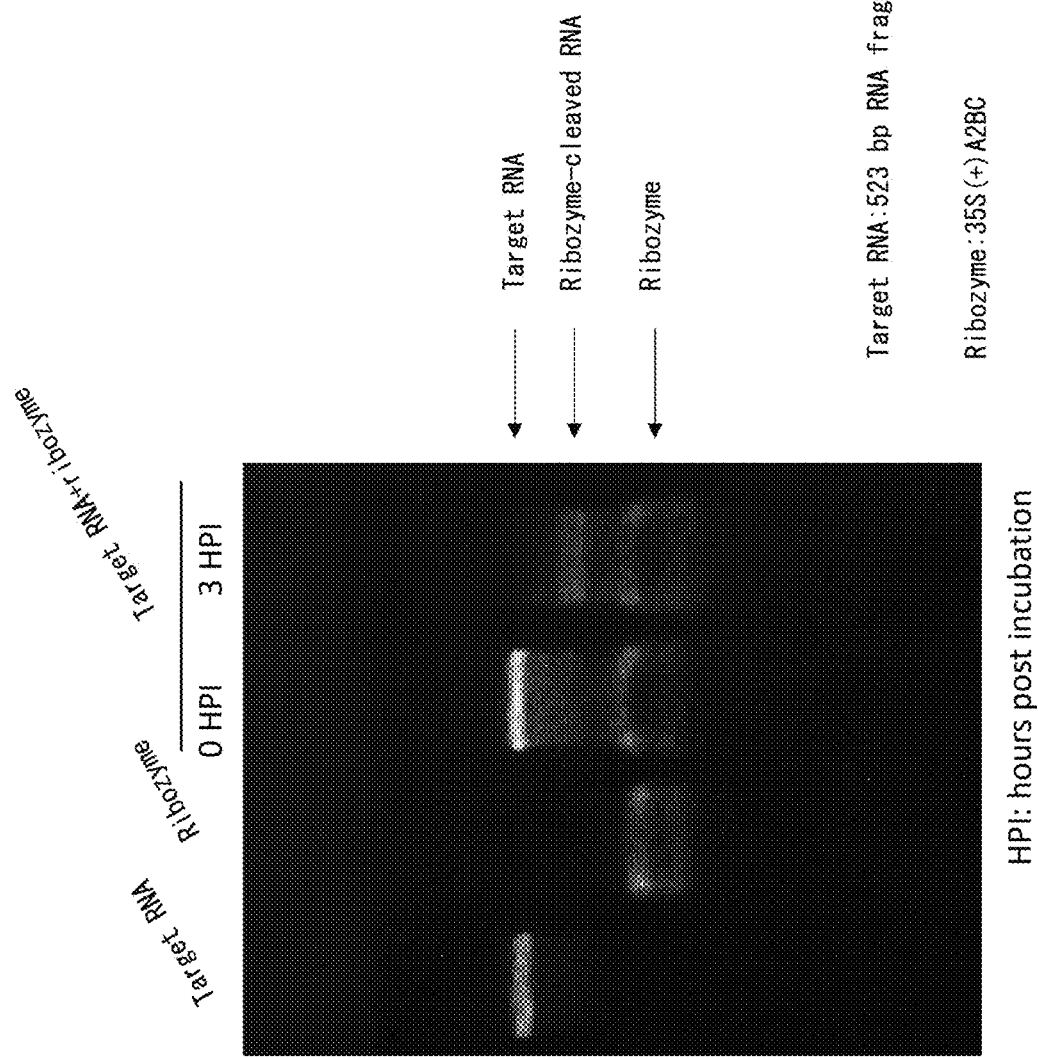
FIG. 12 shows the results of examining the in vitro cleavage activity of the ribozyme expressed in *Arabidopsis thaliana*.

PCR amplification was carried out using primers having the T7 promoter sequence added to the 35S promoter sequence and the ribozyme 35S (+)-A2BC, respectively (35S promoter sequence forward primer: 5'-CTAATACGACTCACTATAGGGAGACAGCTATGAC-CATGATTACGCCAAGC-3' (SEQ ID NO: 15); 35S promoter sequence reverse primer: 5'-ACCATG-GATCCTCTAGAGTCGACTG-3' (SEQ ID NO: 16); ribozyme 35S (+)-A2BC forward primer: 5'-CTAATACGACTCACTATAGGGAGAAGTAGTGAT-TGGGCGGAC-3' (SEQ ID NO: 17); ribozyme 35S (+)-A2BC reverse primer: 5'-CGCCATTGGGATGAGCTCAA-3' (SEQ ID NO: 18)), and the obtained PCR product was used as template for transcription with T7 RNA polymerase (CUGA7 in vitro transcription kit). After denaturation treatment of 10 μg of ribozyme transcription product in 50 μL of reaction mixture (50 mM Tris-HCl) at 95° C. for 2 minutes, rapid cooling and then addition of MgCl₂ to a final concentration of 50 mM, it was incubated at 37° C. for 3 hours for auto-cleavage of the cis-form ribozyme. In 10 μL of reaction mixture with addition of Tris-HCl to a final concentration of 50 mM, 2.1 μg of monomerized ribozyme was added with respect to 900 ng of 35S promoter RNA fragment, and the mixture was denatured at 95° C. for 2 minutes and rapidly cooled. The reaction was initiated by addition of MgCl₂ (final concentration: 50 mM), and was followed by incubation at 37° C. for 3 hours to cleave the 35S promoter RNA fragment by the trans form ribozyme (FIG. 12).

[Experiment 8] Creation of Ribozyme-Introduced *Arabidopsis thaliana*

Figure 13:
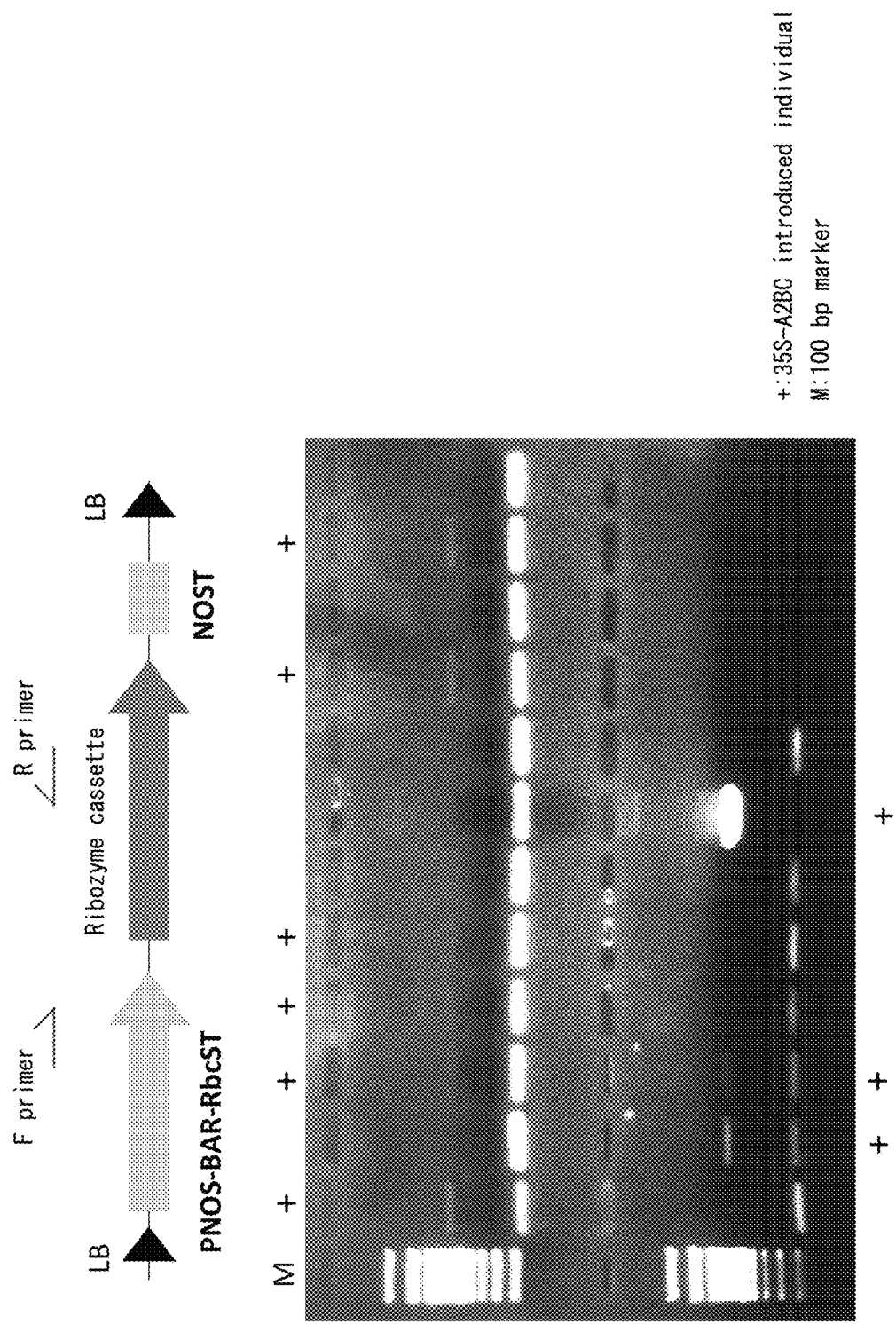
FIG. 13 shows the results of PCR detection of the ribozyme A2BC cassette that has been introduced into an *Arabidopsis thaliana* Col-0 GFP-TGS line. The upper level in the electrophoresis photograph shows the locations of the PCR primers used to confirm the presence or absence of ribozyme incorporated into the plant transformants. The lower level lane shows the different recombinant individuals. The "+" symbol indicates that ribozyme was confirmed.

In order to examine the effect of scaffold RNA-cleaving ribozyme with introduction by gene recombination, first a line having the 35S promoter region of GFP gene methylated was created. A construct incorporating the GFP gene downstream from the 35S promoter of expression vector pBE2113 was prepared, and introduced into an *Arabidopsis thaliana* Col-0 line by the *Agrobacterium* method. The transformants were screened on kanamycin (50 μg/ml) medium. Next, a line with introduction of at least 3 copies and excess expression levels of the GFP gene, resulting in induced methylation of the 35S promoter and essentially inhibited GFP gene expression (Col-0 GFP-TGS) in the T4 generation, was screened out from among the transformed individuals (T1 generation). The ribozyme expression vector constructed in Experiment 6 was introduced into this Col-0 GFP-TGS line by the *Agrobacterium* method. Screening of transformants was carried out by spraying 0.01% BASTA at about 2 weeks after inoculation. Since false positive individuals tend to be found in screening by BASTA spraying, DNA was extracted from the selected individuals by a common method and the extracted DNA was treated by PCR using a primer pair consisting of ribo-insert-check-F (5'-CCCCTAAGTGGGATATTAAGTCAAG-3': SEQ ID NO: 19) and ribo-insert-check-R (5'-TATCCCACT-TAGGGGTTTGGAAAC-3': SEQ ID NO: 20), to confirm introduction of the ribozyme 35S-A2BC (FIG. 13).

Figure 14:
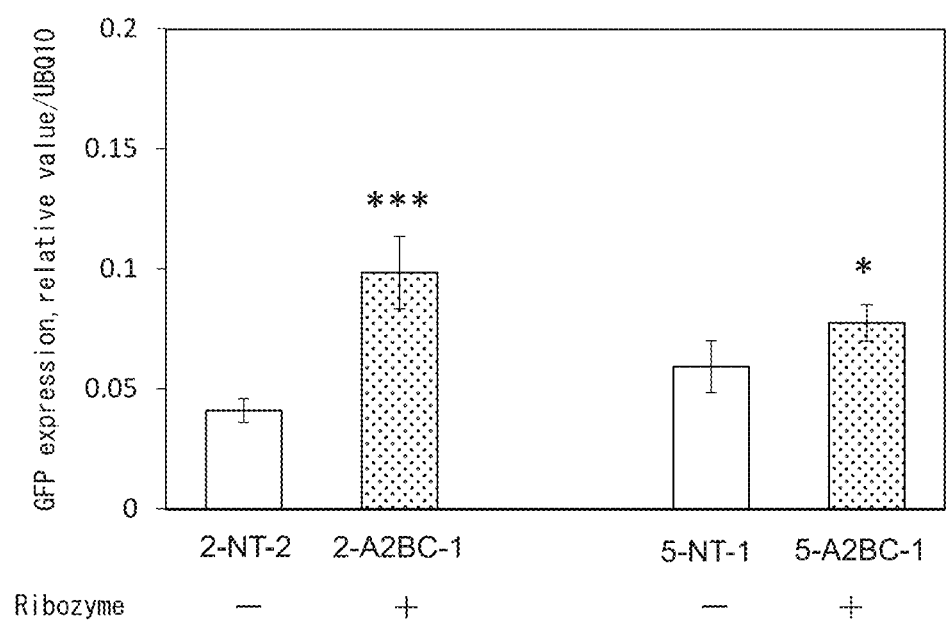
FIG. 14 shows changes in the GFP gene expression in a ribozyme-expressing *Arabidopsis thaliana* Col-0 GFP-TGS line.

[Experiment 9] Expression Analysis of GFP Gene for Ribozyme-Introduced Col-0 GFP-TGS Individuals In the ribozyme 35S-A2BC-introduced T1 individuals obtained in Experiment 8, it is expected that demethylation of the 35S promoter region is induced by ribozyme cleavage of the scaffold RNA plus strand of 35S promoter, thereby increasing the expression level of the GFP gene. As a result of comparing GFP gene expression levels between the ribozyme 35S-A2BC-expressing individuals and non-expressing individuals, it was confirmed that GFP expression had increased by a maximum of about 2-fold in the ribozyme 35S-A2BC-expressing individuals compared to the non-expressing individuals (FIG. 14). The GFP gene expression levels were measured by quantitative RT-PCR (GeXP expression analysis system, AB Science) with the total RNA extracted from leaves using RNAzol RT (Molecular Research Center). The gene used as the internal standard was the UBQ10 gene, and the primer pairs used for RT-PCR of the GFP and UBQ10 genes were GeXP-GFP-F (5'-AGGTGACACTATAGAATATATATCATGGCCGAC-AAGCA-3': SEQ ID NO: 21), GeXP-GFP-R (5'-GTACGACTCACTATAGGGATGGGTGCTCAGGTA-GTGGTT-3': SEQ ID NO: 22) and GeXP-Atubq10-F (5'-AGGTGACACTATAGAATATTGGCCGACTACAACAT-TCA-3': SEQ ID NO: 23), GeXP-Atubq10-R (5'-GTACGACTCACTATAGGGAAAGTGATGGTCTTTC-CGGTG-3': SEQ ID NO: 24), respectively.

The invention claimed is:

1. A method for inhibiting methylation of a 35S promoter in a plant cell, wherein the method comprises cleaving a scaffold RNA produced by transcription of the 35S promoter in an RNA-directed DNA methylation mechanism in the plant cell;
wherein the scaffold RNA is cleaved by expressing one or more ribozymes specific for the scaffold RNA,
the one or more ribozymes is introduced into the plant cell by a plant virus vector method or an agroinfiltration method, and
the plant is a Poaceae, Leguminosae, Brassicaceae, Compositae, Solanaceae, Rosaceae, Cucurbitaceae, or Convolvulaceae plant.

2. The method according to claim 1, wherein expression of the one or more ribozymes is transient.

3. The method according to claim 1, wherein the plant cell is a non-isolated cell of a plant body.

4. The method according to claim 1, wherein the plant cell is a cultured cell.

5. The method according to claim 1, wherein the plant virus vector method is carried out by using a plant virus vector derived from Tobacco mosaic virus (TMV), Cucumber mosaic virus (CMV), Potato X virus (PVX), Clover yellow vein virus (ClYVV), Bean yellow dwarf virus (BeYDV), Beet curly top virus (BCTV), Cabbage leaf-curl virus (CaLCuV), Wheat dwarf virus (WDV), Tomato yellow leaf curl China virus (TYLCCNV), or Cauliflower mosaic virus (CaMV).

6. The method of claim 1, wherein the plant is selected from the group consisting of alfalfa, barley, green bean, canola, cowpea, cotton, corn, clover, lotus, lentil, lupin, millet, oat, pea, peanut, rice, rye, sweet clover, sunflower, sweet pea, soybean, sorghum, triticale, jicama, velvet bean, horse-bean, wheat, *Wisteria*, nut plants, thale cress, redtop grass, Welsh onion, snapdragon, dutch celery, peanut, asparagus, *Atropa*, wild oat, thorny bamboo, rape, bromegrass, rurimagaribana, *camellia, cannabis, capsicum*, chickpea, goosefoot, chicory, citrus, coffee tree, juzudama, cucumber, pumpkin, bermudagrass, *dactylis*, jimsonweed, *digitalis*, yam, oil palm, ooshiba, fescue, strawberry, geranium, soybean, sunflower, Hemerocallidoideae, Para rubber plant, henbane, sweet potato, lettuce, *Lens culinaris*, lily, flax, ryegrass, lotus, tomato, marjoram, apple, mango, *Manihot*, burr medic, African toadflax, tobacco, *Onobrychis*, geranium, Chinese fountain grass, *Petunia, Phleum*, meadow grass, cherry flower, buttercup, radish, currant, castor bean, raspberry, sugarcane, *Salpiglossis, Senecio, Setaria*, white mustard, eggplant, sorghum, buffalo grass, cacao, clover, *Trigonella caerulea* and grape.

* * * * *

SEQUENCE LISTING

<160> NUMBER OF SEQ ID NOS: 24

<210> SEQ ID NO 1
<211> LENGTH: 362
<212> TYPE: DNA
<213> ORGANISM: Cauliflower mosaic virus

<400> SEQUENCE: 1

```
ccaaagggca attgagactt ttcaacaaag gtaatatcc ggaaacctcc tcggattcca      60
ttgcccagct atctgtcact ttattgtgaa gatagtggaa aaggaaggtg gctcctacaa    120
atgccatcat tgcgataaag gaaaggccat cgttgaagat gcctctgccg acagtggtcc    180
caaagatgga cccccaccca cgaggagcat cgtggaaaaa gaagacgttc caaccacgtc    240
ttcaaagcaa gtggattgat gtgatatctc cactgacgta agggatgacg cacaatccca    300
ctatccttcg caagaccctt cctctatata aggaagttca tttcatttgg agagaacacg    360
gg                                                                    362
```

<210> SEQ ID NO 2
<211> LENGTH: 345
<212> TYPE: DNA
<213> ORGANISM: Cauliflower mosaic virus

<400> SEQUENCE: 2

```
tctctccaaa tgaaatgaac ttccttatat agaggaaggg tcttgcgaag gatagtggga     60
ttgtgcgtca tcccttacgt cagtggagat atcacatcaa tccacttgct ttgaagacgt    120
ggttggaacg tcttcttttt ccacgatgct cctcgtgggt ggggtccat ctttgggacc     180 actgtcggca gaggcatctt caacgatggc ctttccttta tcgcaatgat ggcatttgta    240
ggagccacct cctttttcca ctatcttcac aataaagtga cagatagctg ggcaatggaa    300
tccgaggagg tttccggata ttacccttg ttgaaaagtc tcaat                     345
```

<210> SEQ ID NO 3
<211> LENGTH: 57
<212> TYPE: DNA
<213> ORGANISM: Artificial Sequence
<220> FEATURE:
<223> OTHER INFORMATION: Ribozyme for 35S promoter (antisense)

<400> SEQUENCE: 3

```
cgaggcctga tctccactct gatgagtccg tgaggacgaa acgtaaggac gcgtgcg       57
```

<210> SEQ ID NO 4
<211> LENGTH: 1172
<212> TYPE: DNA
<213> ORGANISM: Nicotiana benthamiana 16c

<400> SEQUENCE: 4

```
actctgaaaa gttgtttccc attataggcc tttggaggag cctaaggtaa cgggtcgata     60
gacagtgaaa taacacttct atcaccttt ccttccaccg aggatgttta cggtagtaac    120
gctatttcct ttccggtagc aacttctacg gagacggctg tcaccagggt ttctacctgg    180
gggtgggtgc tcctcgtagc acctttttct tctgcaaggt tggtgcagaa gtttcgttca    240
cctaactaca ctatagaggt gactgcattc cctactgcgt gttagggtga taggaagcgt    300
tctgggaagg agatatattc cttcaagtaa agtaaacctc tcttgtgccc cctgagatct    360
cctaggttcc tctatattgt tacttctgat tagaaaaaga gaaagagtag aaaagtgaag    420
aggatagtaa taggagccgg cttaagtcat ttcctcttct tgaaaagtga cctcaacagg    480
```

```
gttaagaaca acttaatcta ccactacaat tacccatgtt taaaagacag tcacctctcc      540
cacttccact acgttgtatg cctttgaat gggaatttaa ataaacgtga tgaccttttg       600
```

```
gttaagaaca acttaatcta ccactacaat tacccatgtt taaaagacag tcacctctcc      540
cacttccact acgttgtatg cctttgaat gggaatttaa ataaacgtga tgaccttttg       600
atggacaagg taccggttgt gaacagtgat gaaagagaat accacaagtt acgaaaagtt      660
ctatgggtct agtatacttc gccgtgctga agaagttctc gcggtacgga ctccctatgc      720
acgtcctctc ctggtagaag aagttcctgc tgcccttgat gttctgtgca cgacttcagt      780
tcaaactccc tctgtgggag cagttgtcct agctcgaatt cccttagcta agttcctcc       840 tgcctttgta ggagccggtg ttcaacctta tgttgatgtt gagggtgttg catatgtagt      900
accggctgtt cgttttcttg ccgtagtttc ggttgaagtt ctgggcggtg ttgtagcttc      960
tgccgccgca cgttgagcga ctagtaatag ttgttttatg aggttaaccg ctaccgggac     1020
aggaaaatgg tctgttggta atggacaggt gtgttagacg ggaaagcttt ctagggttgc     1080
ttttctctct ggtgtaccag gaagaactca aacattgtcg acgacccta tgtgtaccgt      1140 acctacttga tatgtttgta ctactcgaaa tt                                   1172
```

<210> SEQ ID NO 5
<211> LENGTH: 385
<212> TYPE: DNA
<213> ORGANISM: Cauliflower mosaic virus

<400> SEQUENCE: 5

```
ctctagagga tccccctca gaagaccaga gggctattga acttttcaa caaagggtaa       60 tatcgggaaa cctcctcgga ttccattgcc cagctatctg tcacttcatc gaaaggacag     120
tagaaaagga aggtggctcc tacaaatgcc atcattgcga taaggaaag gctatcgttc      180 aagatgcctc taccgacagt ggtcccaaag atggaccccc acccacgagg aacatcgtgg     240
aaaaagaaga cgttccaacc acgtcttcaa agcaagtgga ttgatgtgat atctccactg     300
acgtaaggga tgacgcacaa tcccactatc cttcgcaaga cccttcctct atataaggaa     360
gttcatttca tttggagagg acagg                                           385
```

<210> SEQ ID NO 6
<211> LENGTH: 739
<212> TYPE: DNA
<213> ORGANISM: Artificial Sequence
<220> FEATURE:
<223> OTHER INFORMATION: Ribozyme 35S(+)A cassette

<400> SEQUENCE: 6

```
aagcttcttt ttttcttctt cttcgttcat acagttttt tttgtttatc agcttacatt       60
ttcttgaacc gtagctttcg tttcttctt tttaactttc cattcggagt tttgtatct      120 tgtttcatag tttgtcccag gattagaatg attaggcatc gaaccttcaa gaatttgatt    180
gaataaaaca tcttcattct taagatatga agataatctt caaaaggccc ctgggaatct    240
gaaagaagag aagcaggccc atttatatgg gaaagaacaa tagtatttct tatataggcc    300
catttaagtt gaaaacaatc ttcaaaagtc ccacatcgct tagataagaa acgaagctg     360 agttttatata cagctagagt cgaagtagtg attgggcgga ccgttgacga aacgcgaaag   420
cgtctagcga aagctactga tgagtcgacc gatgaagtct gatgagtccg aaaggacgaa    480
acagatagcc ggaccgttga cgaaacgcga aagcgtctag cgaaagctac tgatgagtcg    540
acctttggct gatgagtccg aaaggacgaa accactgtcc ggaccgttga cgaaacgcga    600
aagcgtctag cgaaagctac tgatgagtcg acgctttgaa ctgatgagtc cgaaaggacg    660
```

```
aaacgtggtt gcggaccgtt gacgaaacgc gaaagcgtct agcgaaagct actgatgagt    720
cgaccttttt tttgagctc                                                 739
```

<210> SEQ ID NO 7
<211> LENGTH: 24
<212> TYPE: DNA
<213> ORGANISM: Artificial Sequence
<220> FEATURE:
<223> OTHER INFORMATION: 35S-346F-bisuT primer

<400> SEQUENCE: 7

```
attgagaytt ttyaayaaag ggta                                            24
```

<210> SEQ ID NO 8
<211> LENGTH: 22
<212> TYPE: DNA
<213> ORGANISM: Artificial Sequence
<220> FEATURE:
<223> OTHER INFORMATION: 35S+1A-bisuA primer

<400> SEQUENCE: 8

```
ctctccaaat gaaatgaact tc                                              22
```

<210> SEQ ID NO 9
<211> LENGTH: 20
<212> TYPE: DNA
<213> ORGANISM: Artificial Sequence
<220> FEATURE:
<223> OTHER INFORMATION: T7-35S-5-345 primer

<400> SEQUENCE: 9

```
attgagactt ttcaacaaag                                                 20
```

<210> SEQ ID NO 10
<211> LENGTH: 22
<212> TYPE: DNA
<213> ORGANISM: Artificial Sequence
<220> FEATURE:
<223> OTHER INFORMATION: 35S+1R primer

<400> SEQUENCE: 10

```
gttctctcca aatgaaatga ac                                              22
```

<210> SEQ ID NO 11
<211> LENGTH: 21
<212> TYPE: DNA
<213> ORGANISM: Artificial Sequence
<220> FEATURE:
<223> OTHER INFORMATION: 35S-3-130 primer

<400> SEQUENCE: 11

```
gcagaggcat cttcaacgat g                                               21
```

<210> SEQ ID NO 12
<211> LENGTH: 21
<212> TYPE: DNA
<213> ORGANISM: Artificial Sequence
<220> FEATURE:
<223> OTHER INFORMATION: 35S-5-160 primer

<400> SEQUENCE: 12

```
ccacccacga ggagcatcgt g                                               21
```

<210> SEQ ID NO 13
<211> LENGTH: 45

-continued

<210> SEQ ID NO 13
<211> LENGTH: 45 (implied)
<212> TYPE: DNA
<213> ORGANISM: Artificial Sequence
<220> FEATURE:
<223> OTHER INFORMATION: 35S(-)-5RZ-45

<400> SEQUENCE: 13
cgaggcctga tctccactct gatgagtccg tgaggacgaa acgta        45

<210> SEQ ID NO 14
<211> LENGTH: 32
<212> TYPE: DNA
<213> ORGANISM: Artificial Sequence
<220> FEATURE:
<223> OTHER INFORMATION: 35S(-)-3RZ-32

<400> SEQUENCE: 14
cgcacgcgtc cttacgtttc gtcctcacgg ac        32

<210> SEQ ID NO 15
<211> LENGTH: 50
<212> TYPE: DNA
<213> ORGANISM: Artificial Sequence
<220> FEATURE:
<223> OTHER INFORMATION: 35S-promoter-F primer

<400> SEQUENCE: 15
ctaatacgac tcactatagg gagacagcta tgaccatgat tacgccaagc        50

<210> SEQ ID NO 16
<211> LENGTH: 25
<212> TYPE: DNA
<213> ORGANISM: Artificial Sequence
<220> FEATURE:
<223> OTHER INFORMATION: 35S-promoter-R primer

<400> SEQUENCE: 16
accatggatc ctctagagtc gactg        25

<210> SEQ ID NO 17
<211> LENGTH: 42
<212> TYPE: DNA
<213> ORGANISM: Artificial Sequence
<220> FEATURE:
<223> OTHER INFORMATION: 35S(+)-A2BC-F primer

<400> SEQUENCE: 17
ctaatacgac tcactatagg gagaagtagt gattgggcgg ac        42

<210> SEQ ID NO 18
<211> LENGTH: 20
<212> TYPE: DNA
<213> ORGANISM: Artificial Sequence
<220> FEATURE:
<223> OTHER INFORMATION: 35S(+)-A2BC-R primer

<400> SEQUENCE: 18
cgccattggg atgagctcaa        20

<210> SEQ ID NO 19
<211> LENGTH: 25
<212> TYPE: DNA
<213> ORGANISM: Artificial Sequence
<220> FEATURE:
<223> OTHER INFORMATION: ribo-insert-check-F primer

<400> SEQUENCE: 19

```
ccccctaagtg ggatattaag tcaag                                          25

<210> SEQ ID NO 20
<211> LENGTH: 24
<212> TYPE: DNA
<213> ORGANISM: Artificial Sequence
<220> FEATURE:
<223> OTHER INFORMATION: ribo-insert-check-R primer

<400> SEQUENCE: 20
tatcccactt aggggtttgg aaac                                            24

<210> SEQ ID NO 21
<211> LENGTH: 38
<212> TYPE: DNA
<213> ORGANISM: Artificial Sequence
<220> FEATURE:
<223> OTHER INFORMATION: GeXP-GFP-F primer

<400> SEQUENCE: 21
aggtgacact atagaatata tatcatggcc gacaagca                             38

<210> SEQ ID NO 22
<211> LENGTH: 39
<212> TYPE: DNA
<213> ORGANISM: Artificial Sequence
<220> FEATURE:
<223> OTHER INFORMATION: GeXP-GFP-R primer

<400> SEQUENCE: 22
gtacgactca ctatagggat gggtgctcag gtagtggtt                            39

<210> SEQ ID NO 23
<211> LENGTH: 38
<212> TYPE: DNA
<213> ORGANISM: Artificial Sequence
<220> FEATURE:
<223> OTHER INFORMATION: GeXP-Atubq10-F primer

<400> SEQUENCE: 23
aggtgacact atagaatatt ggccgactac aacattca                             38

<210> SEQ ID NO 24
<211> LENGTH: 39
<212> TYPE: DNA
<213> ORGANISM: Artificial Sequence
<220> FEATURE:
<223> OTHER INFORMATION: GeXP-Atubq10-R primer

<400> SEQUENCE: 24
gtacgactca ctatagggaa agtgatggtc tttccggtg                            39
```